(12) United States Patent
Sakiguchi et al.

(10) Patent No.: US 7,223,799 B2
(45) Date of Patent: May 29, 2007

(54) COLOR-DEVELOPING COMPOSITION AND COSMETIC, FRAGRANCE PRODUCTS AND MISCELLANEOUS GOODS FOR DISPLAY WITH THE USE OF THE SAME

(75) Inventors: Takayuki Sakiguchi, Yokohama (JP); Norinobu Yoshikawa, Yokohama (JP); Keiko Sakai, Yokohama (JP); Makio Akimoto, Yokohama (JP); Kazuhisa Ohno, Yokohama (JP); Hiroshi Fukui, Yokohama (JP)

(73) Assignee: Shiseido Research Center, Kanagawa (JP)

( * ) Notice: Subject to any disclaimer, the term of this patent is extended or adjusted under 35 U.S.C. 154(b) by 240 days.

(21) Appl. No.: 10/312,357

(22) PCT Filed: Mar. 29, 2002

(86) PCT No.: PCT/JP02/03141

§ 371 (c)(1),
(2), (4) Date: Dec. 26, 2002

(87) PCT Pub. No.: WO02/078664

PCT Pub. Date: Oct. 10, 2002

(65) Prior Publication Data

US 2003/0190295 A1    Oct. 9, 2003

(30) Foreign Application Priority Data

Mar. 30, 2001  (JP) .............................. 2001-102732
Jun. 5, 2001   (JP) .............................. 2001-169880

(51) Int. Cl.
  *B01F 3/12*   (2006.01)
  *C01B 33/14*  (2006.01)
  *F21V 9/00*   (2006.01)

(52) U.S. Cl. ........................................ 516/34; 252/587
(58) Field of Classification Search ................ 252/587; 516/34
See application file for complete search history.

(56) References Cited

U.S. PATENT DOCUMENTS

| | | | | |
|---|---|---|---|---|
| 3,150,048 A | * | 9/1964 | Hollub et al. | .................. 424/61 |
| 3,586,417 A | | 6/1971 | Fields | |
| 4,411,933 A | * | 10/1983 | Samejima et al. | ........ 427/213.3 |
| 4,611,008 A | * | 9/1986 | Heinzelmann | .............. 514/470 |
| 5,328,683 A | * | 7/1994 | Harashima | ................... 424/63 |
| 5,783,176 A | * | 7/1998 | Meiring et al. | ................ 424/64 |
| 6,121,243 A | * | 9/2000 | Lanzendorfer et al. | ........ 514/28 |
| 6,207,174 B1 | * | 3/2001 | Hineno et al. | .............. 424/401 |

FOREIGN PATENT DOCUMENTS

| | | |
|---|---|---|
| JP | 63-59422 | 7/1980 |
| JP | 57-26611 A | 2/1982 |
| JP | 59-105073 A | 6/1984 |
| JP | 59-163306 | 9/1984 |
| JP | 03-044309 | 2/1991 |
| JP | 04-308518 | 10/1992 |
| JP | 5-112431 A | 5/1993 |
| JP | 06-192527 | 7/1994 |
| JP | 08-012319 | 1/1996 |
| JP | 10-59742 A | 3/1998 |
| JP | 10-120524 | 5/1998 |
| JP | 2001-206712 | 7/2001 |

OTHER PUBLICATIONS

Francis, Alfred W.; Structural Colors in Emulsions; J. Phys. Chem; 1952; vol. 56, No. 4, p. 510-513.
Holmes, Harry N. et al.; Chromatic Emulsions; J. Am. Chem. Soc.; Jan. 1922; vol. 44, No. 1, p. 71-74.
Supplementary European Search Report, dated Jan. 28, 2005.

* cited by examiner

*Primary Examiner*—Randy Gulakowski
*Assistant Examiner*—Timothy J. Kugel
(74) *Attorney, Agent, or Firm*—Fei-Fei Chao; Andrews Kurth LLP

(57) ABSTRACT

The invention provides a color-developing composition without using a pigment or dye and capable of being colored sustainably and stably after mixing two liquid phases which are colorless before mixing. The composition consists of two discrete liquid phases, wherein the refractive index of each liquid phase is identical to each other at a point within the wavelength range from 400 nm to 800 nm, wherein a continuous layer and a dispersion layer are formed by mixing and dispersing said two phases whereby developing a color. Alternatively, the composition is a powder dispersion consisting of a liquid phase and a silica powder-containing solid phase, wherein said liquid phase has a refractive index n1 and said silica has a refractive index n2, which satisfy Equation (1):

$$|n1-n2|<0.05 \qquad (1)$$

whereby developing a color on the basis of the difference in the refractive index at the interface between the liquid phase and the solid phase. The present invention also provides a cosmetic preparation, a fragrance product and a display article using the composition.

12 Claims, 15 Drawing Sheets

Wavelength dependency of refractive index of two phases

COLOR-DEVELOPING COMPOSITION AND COSMETIC, FRAGRANCE PRODUCTS AND MISCELLANEOUS GOODS FOR DISPLAY WITH THE USE OF THE SAME

RELATED APPLICATIONS

This application claims the priority of Japanese Patent Application Nos. 2001-102732 filed on Mar. 30, 2001 and 2001-169880 filed on Jun. 5, 2001, which are incorporated herein by references.

FIELD OF THE INVENTION

The present invention relates to a color-developing composition, and a cosmetic preparation, a fragrance product and a display article using the color-developing composition; and, in particular, to a technique for developing a color based on only slight difference in the refractive index of two phases and on the wavelength dependency and to improvement thereof.

BACKGROUND OF THE INVENTION

A liquid composition being a constituent of a cosmetic product such as a fragrance product like perfume or cologne, such as an enamel remover, should be colored appropriately for promoting its attractive appearance. For example, a fragrance product has been colored so far with a colorant such as a pigment or dye, since it should be characterized not only by its aroma, effectiveness and usability but also by its appearance for the purpose of emphasizing its uniqueness. In response to a further diversity of the consumer's demand, in addition to just coloring itself, a fragrance product whose appearance was further characterized was developed. Thus, it was a 2-phase type fragrance product wherein there were two liquid phases separated from each other and colored with colorants such as die and pigment to have different color, and when the phases were mixed and dispersed, the product could exhibit the mixed color.

Otherwise, such a color development can also be accomplished by utilizing the difference in the refractive index between the two phases. Thus, Francis et al reported the phenomenon called "chromatic emulsion" in J. Phys. Chem. in 1952. In this phenomenon, an aurora-like beautiful color is developed when the difference is small in the refractive index between an oil phase and an aqueous phase in a surfactant-supplemented liquid-liquid emulsified dispersion.

Nevertheless, when a color is imparted using a pigment as a colorant, it is difficult to provide a transparent pigment-containing dispersion because of too large difference in the refractive index between the pigment and the dispersion medium which leads to a turbidness, although the color is intense and the color tone is bright. The specific gravity of a pigment which is often high may also allow the sedimentation to occur readily, resulting in a difficulty in re-dispersing.

On the other hand, when a dye is employed as a colorant for imparting a color, its solution poses a problem due to the adhesion to a skin or clothes and it is difficult to be washed off once adhered, although it allows the color adjustment to be accomplished easily. In addition, some dyes involved are problematically hazardous to human health, and are subjected to the limitation of use. Moreover, the weatherability of a pigment or dye, especially of an organic dye, is problematic, and the discoloration under a light such as sunlight or fluorescent lamp leads to a poor stability during storage.

The 2-phase fragrance product described above, which employs a colorant, also posed the problems due to the colorant, such as a discoloration depending on the stability of the colorant. While a 2-phase fragrance product can be imparted with a further aspect if it develops a color upon mixing though it is a colorless before mixing, such an aspect is difficult to be imparted when using a colorant.

In the method for developing a color utilizing the difference in the refractive index between two phases, since the dispersion system employed is a liquid-liquid system in which particles were formed by emulsifying the system in the presence of a surfactant, the system undergoes a sustained deterioration of the emulsion system due to aggregation, coalescence or the like, resulting in a problem in applications where the color development should be maintained stably.

SUMMARY OF THE INVENTION

In view of the problems described above, the first objective of the invention is to provide a color-developing composition capable of developing a color without using a pigment or dye and capable of being colored once after mixing the two liquid phases which are colorless before mixing. The second objective of the invention is to provide a color-developing composition capable of developing a sustainable stable color without using a pigment or dye.

For the purpose of achieving the objectives described above, we made every effort and finally discovered that a color can be developed by mixing and dispersing two discrete transparent liquid phases whose refractive indexes are different only slightly from each other.

We also discovered that a composition obtained by dispersing a silica powder in a medium whose refractive index is different only slightly from that of said silica is capable of developing a color stably and sustainably, whereby establishing the invention.

Namely, a color-developing composition of the present invention for the first objective mentioned above consists of two discrete liquid phases, wherein the refractive index of each liquid phase is identical to each other at a point within the wavelength range from 400 nm to 800 nm, wherein a continuous layer and a dispersion layer are formed by mixing and dispersing said two phases whereby developing a color.

In the composition, it is preferable that the absolute refractive indexes of the respective liquid phases at the wavelength of sodium D ray, n1 and n2, are 1.3 or higher.

In the composition, it is preferable that one of the two discrete liquid phase contains water and/or a lower alcohol.

In the composition, it is preferable that one of the two discrete liquid phase contains a silicone oil.

In the composition, it is preferable that one or both of the two discrete liquid phase contain perfumes.

A color-developing composition of the present invention for the second objective mentioned above is a powder dispersion consisting of a liquid phase and a silica powder-containing solid phase, wherein said liquid phase has a refractive index n1 and said silica has a refractive index n2, which satisfy Equation (1):

$$|n1-n2|<0.05 \qquad (1)$$

whereby developing a color on the basis of the difference in the refractive index at the interface between the liquid phase and the solid phase.

In the composition, it is preferable that said liquid phase consists of one or more substances selected from the group consisting of oils, fats and fatty oils, waxes, alcohols and water.

In the composition, it is preferably a powder dispersion gel or a powder dispersion liquid crystal employing a gel phase or a liquid crystal phase consisting of one or more substances selected from the group consisting of oils, fats and fatty oils, waxes, alcohols and water instead of said liquid phase.

In the composition, the silica powder has preferably a spherical shape.

In the composition, the mean particle size of the silica powder is preferably 0.1 μm to 200 μm.

In the composition, the silica powder is preferably contained in an amount of 0.01 to 60% by mass based on the entire composition.

The composition of the invention is preferably used in a cosmetic preparation such as a skin care product, make-up product, fragrance product, skin or hair cleansing product or enamel removing product, or used in a display article.

According to a color-developing composition of the invention described above, without using a colorant, a clear color can be developed by mixing and dispersing two discrete colorless and transparent liquid phases.

Also by utilizing the very slight difference in the refractive index between the silica powder and the liquid phase, without adding a colorant, a color-developing composition developing a clear color sustainably and stably can be obtained.

When such a color-developing composition is applied to a cosmetic product, fragrance product and an product employed as a display article, it can impart a highly sophisticated design to the products, whereby serving as a widely utilizable composition.

BEST MODES FOR CARRYING OUT THE INVENTION

The present invention is further described below in detail. In the invention, two homogeneous liquids forming discrete two phases are charged into a suitable container, allowed to stand to form a two-phase colorless transparent liquid composition, and mixed and dispersed by shaking the container with a hand gently to allow one phase to be dispersed in the other phase, whereby developing a color as a whole.

Figure 1:
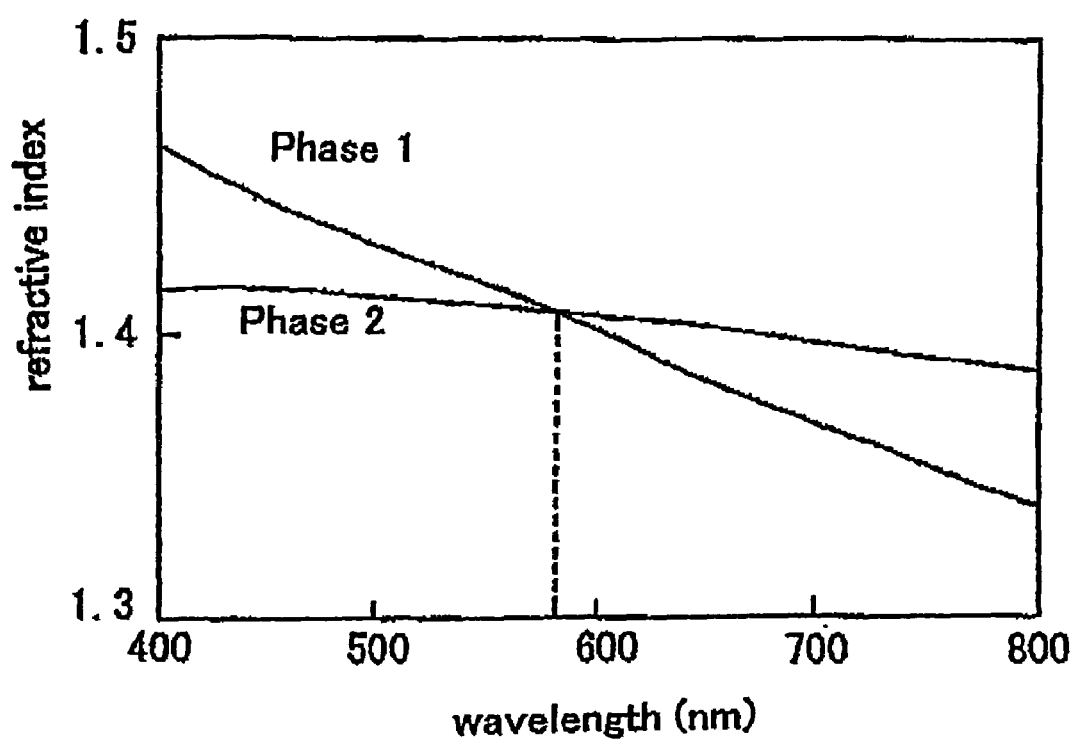
FIG. 1 shows a graph indicating a wavelength dependency of the refractive indexes of the both liquid phases of a color-developing composition according to the invention.

The color obtained by this process is considered, as shown in FIG. 1, to be resulted from the difference in the refractive index between Phase 1 and Phase 2, and the agreement in the refractive index at a certain wavelength within the visual light range (400 nm to 800 nm).

As an example, as shown in FIG. 1, a case where the two refractive indexes, one is the refractive index of Phase 1 which becomes lower as the wavelength is longer, and the other is the refractive index of Phase 2 which does not depend on wavelength so much, are in agreement at 580 nm is considered here.

When these two phases were mixed and dispersed, the 580 nm light can transmit but other wavelength lights are scattered due to the difference in the refractive index although the degree of the scattering may vary.

As a result, the 580 nm light serves as a transmitting light to allow a yellow color to be observed, while its complementary color becomes a scattering light. This scattering color differs depending on the angle, and exhibits different colors depending on the angle at which it is observed, resulting in a shining color.

When Phase 1 is not changed and Phase 2 is changed in such a manner that the overall refractive index becomes higher, the transmitting light shifts to blue, and thereafter becomes white-turbid at a further higher index, thus explaining the phenomenon we observed.

While the transmitting light of this mixture may change depending on temperature, such a change is due to the temperature dependency of the refractive index.

The wavelength dependency of the refractive index can be measured using an ellipsometer. The transmitting light when the two phases are mixed can be measured using a spectrophotometer.

The dispersion thus colored recovers its initial form which is a two-phase colorless transparent liquid composition after a certain time period, and then can be allowed to develop the color again by mixing and dispersing.

In order to effect the color development phenomenon described above satisfactorily, it is preferable that the absolute refractive indexes of the respective liquid phases at the wavelength of sodium D ray, n1 and n2, are 1.3 or higher.

While in the present invention, it is usual that one of the two liquid phases employed is an aqueous phase and the other is an oil phase, any combination may be employed as long as the two phases are not compatible with each other and separate from each other due to the difference in the polarity between the molecule as a constituent of one liquid phase and the molecule as a constituent of the other liquid phase. For the purpose of exerting the effect of the invention clearly, it is preferable that the transmittance of the white light through a liquid phase whose light path is 1 cm is 95% or higher.

An aqueous phase is not limited particularly and may be like water, lower alcohols and glycols, which may be employed alone or as a mixed solution.

Also, a substance soluble to the aqueous phase such as a moisturizing agent can be added therein. Examples of the moisturizing agent include polyethylene glycol, propylene glycol, glycerin, 1,3-buthylene glycol, hexylene glycol, xylitol, sorbitol, maltitol, chondroitin sulfate, hyaluronic acid, mucoitinsulfuric acid, charonic acid, atelocollagen, cholesteryl 12-hydroxystearete, sodium lactate, bile salt, dl-pyrrolidone carboxylate, short chain soluble collagen, diglyceride☐EO☐PO additive, sixteen night rose extract, yarrow extract and melilot extract.

The oil phase is not limited particularly and may be silicone oils, hydrocarbon oils, ester oils, liquid oils and fats, and higher alcohols, which may be employed alone or in combination. Among these oils, in the view of exerting the effect of the invention, it is preferable that a silicone oil and/or a hydrocarbon oil are added.

Examples of silicone oils include chain polysiloxanes such as methylhydrogenpolysiloxane, dimethylpolysiloxane and methylphenylpolysiloxne; cyclopolysiloxanes such as decamethylpolysiloxane, dodecamethylpolysiloxane and tetramethylhydrogenpolysiloxane; and modified silicones such as fluorine-modified silicone, polyether-modified silicone, alkyl-modified silicone and acryl-modified silicone.

Examples of hydrocarbon oils include liquid paraffin, ozocerite, squalane, pristane, paraffin, ceresin, vaseline and microcrystalline wax.

Examples of ester oils include isopropyl myristate, myristyl myristate, octyl myristate, 2-hexyldecyl myristate, glyceryl trimyristate, cetyl dodecyloctanate, isopropyl palmitate, 2-heptylundecyl palmitate, 2-hexyldecyl palmitate, butyl stearate, isocetyl stearate, 1monoisostearic acid N-alkylgrycol, cholesteryl 2-hydroxystearate, cetostearyl alcohol, trimethylolpropyl triisostearate, pentaerythritol tetra-2-ethylhexanate, glyceryl tri-2-ethylhexanate, cetyl 2-ethylhexanate, 2-ethylhexyl palmitate, ethyleneglycol di-2-ethylhexaenate, trimethylolpropyl tri-2-ethylhexaenate, dipentaerythritol fatty acid ester, isocetyl isostearate, hexyl laurate, decyl oleate, oleyl dioleate, hexyldecyl methyloctanate, cetyl lactate, myristyl lactate, ethyl acetate, butyl acetate, amyl acetate, lanolin acetate, neopentylglycol dicaprate, diisostearyl malate, glyceryl di-2-heptylundecanate, glyceryl tri-2-heptylundecanate, castor oil fatty acid methyl ester, acetoglyceride, diisobutyl adipate, 2-hexyldecyl adipate, di-2-heptylundecyl adipate, ethyl laurate, di-2-ethylhexyl sebacate, isopropyl sebacate, 2-octyldodecyl N-lauroyl-L-glutamate, 2-ethylhexyl succinate, and triethyl citrate.

Examples of liquid fats and fatty oils include avocado oil, Tsubaki oil, evening primrose oil, turtle oil, macademia nut oil, corn oil, mink oil, olive oil, rape seed oil, yolk oil, sesame oil, persic oil, wheat germ oil, sasanqua oil, caster oil, linseed oil, safflower oil, cottonseed oil, perilla oil, soybean oil, peanut oil, tea seed oil, kaya oil, rice bran oil, Chinese paulownia oil, Japanese paulownia oil, Jojoba oil, germ oil, triglycerin, glyceryl trioctanate, and glycerin triisopalmitate.

Examples of higher alcohols include straight chain alcohols such as lauryl alcohol, cetyl alcohol, stearyl alcohol, behenyl alcohol, myristyl alcohol, oleyl alcohol and cetostearyl alcohol; and branch chain alcohols such as monostearyl glyceryl ether(batyl alcohol), 2-decyltetradecanol, lanolin alcohol, cholesterol, phytosterol, hexyldodecanol, isostearyl alcohol and octyldodecanol.

In addition to these oils, a substance soluble to the oil phase such as solid fats and fatty oils, waxes, and higher fatty acids can be added thereto.

Examples of solid fats and fatty oils include hardened oil, cacao butter, coconut oil, hardened coconut oil, horse fat, palm oil, hardened palm oil, beef tallow, hardened beef tallow, nest's-foot oil, beef bone fat, mutton tallow, lard, Japan wax oil, Japan wax kernel oil, and hardened caster oil.

Examples of waxes include beeswax, candelilla wax, cotton wax, carnauba wax, bayberry wax, insect wax, cetaceum, montan wax, rice bran wax, lanolin, lanolin acetate, liquid lanolin, lanolin fatty acid isopropyl, reduced lanolin, hard lanolin, lanolin fatty acid polyethlenegrycol, POE lanolin alcohol ether, POE hydrogenated lanolin alcohol ether, POE lanolin alcohol acetate, POE cholesterol ether, hexyl laurate, sugar cane wax, kapok wax, jojoba wax, and shellac wax.

Examples of higher fatty acids include lauric acid, myristic acid, palmitic acid, stearic acid, behenic acid, oleic acid, 12-hydroxystearic acid, undecylenic acid, tall acid, isostearic acid, linolic acid, linoleic acid, eicosapentaenoic acid, and docosahexaenoic acid.

Also, for the purpose of controlling the rate at which a color-developing dispersion system consisting of a continuous phase and a dispersed phase obtained by mixing two phases recovers again two discrete colorless phases, a surfactant can be used. Examples thereof include anionic surfactants such as fatty acid soaps, ethercarboxylic acids and salts thereof, alkanesulfonates, higher fatty acid ester sulfonates, dialkyl sulfosuccinates, higher fatty acid amide sulfonates, alkylallylsulfonates, higher alcohol sulfate salts, secondary higher alcohol sulfate salts, alkyl and alkylallyl ether sulfate salts, glycerin fatty acid ester sulfate salts, higher fatty acid alkylolamide sulfate salts, sulfated oils, phosphate salts, amino acids, collagen hydrolysate-higher fatty acid condensates, and collagen hydrolysate derivatives; cationic surfactants such as alkylamine salts, polyamine or alkanolamine fatty acid derivatives, alkyltrimethylammonium salts, dialkyldimethylammonium salts, alkyldimethylbenzyl ammonium salts, alkylpyridinium salts, alkylisoquinolinium salts, and dialkylmorpholinium salts; and nonionic surfactants, which may be used as long as the inventive effect is not spoiled.

Further, as long as the inventive effect is not spoiled, materials normally used in cosmetics can be combined, if necessary. For example, ultraviolet absorbers, natural polymers, semi-synthetic polymers, synthetic polymers, inorganic water soluble polymers, thickeners and the like can be used.

Examples of ultraviolet absorbers include p-aminobenzoic acid series ultraviolet absorbers such as p-aminobenzoic acid(PABA), PABA monoglyceride, N,N-dipropoxy-PABA ethyl ester, N,N-diethoxyPABA ethyl ester, N,N-dimethylPABA ethyl ester, and N,N-dimethylPABA butyl ester; anthranilic acid series ultraviolet absorbers such as homomentyl N-acetylanthranilate; salicylic acid series ultraviolet absorbers such as amyl salicylate, menthyl salicylate, monomenthyl salicylate, octyl salicylate, phenyl salicylate, benzyl salicylate, and p-isopropanol phenylsalicylate; cinnamic acid series ultraviolet absorbers such as octyl cinnamate, ethyl 4-isopropylcinnamate, methyl 2,5-diisopropylcinnamate, ethyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethyl hexanoyl di-p-methoxycinnamate, and 3-methyl-4-methylbis(trimethylmethoxy)silylcopthyl 3,4,5-trimethoxycinnamate; benzophenone series ultraviolet absorbers such as 2,4-dihydroxybenzophenone, 2,2'-dihydroxy-4-methoxybenzophenone, 2,2'-dihydroxy-4'-dimethoxybenzophenone, 2,2',4,4'-tetrahydroxybenzophenone, 2-hydroxy-4-methoxy benzophenone, 2-hydroxy-4-methoxy-4'-methylbenzophenone, 2-hydroxy-4-methoxy benzophenone-5-sulfonate, 4-phenylbenzophenone, 2-ethylhexyl-4'-phenylbenzophenone-2-calboxylate, hydroxy-4-n-octoxybenzophenone, and 4-hydroxy-3-carboxybenzophenone; and ultraviolet absorbers such as 3-(4'methylbenzylidene)-d,1-camphor, 3-benzylidene-d,1-camphor, urocanic acid, ethyl urocanate, 2-phenyl-5-methylbenzoxazole, 2,2'-dihydroxy-5-methylphenylbenzotriazol, 2-(2'-hydroxy-5'-t-octylphenyl)benzotriazol, 2-(2'-hydroxy-5'-methylphenyl)benzotriazol, dibenzaladine, dianisoylmethane, 4-methoxy-4'-t-butyl benzoylmethane, and 5-(3,3dimethyl-2-norbornylidene)-3-pentane-2-one.

Examples of natural polymers include plant series polymers such as gum arabic, tragacanth gum, galactan, guar gum, carob gum, karaya gum, carrageenan, pectin, mannan, quinceseed (*Cydonia oblonga*), *Alge colloid* (brown alga extract), and glycyrrhizic acid; microorganizm series polymers such as xanthan gum, dextran, succinoglucan, and pullulan; and animal series polymers such as collagen, casein, albumin, and gelatin.

Examples of semi-synthetic polymers include starch series polymers such as carboxymethylstarch, and methylhydroxypropylstarch; cellulose series polymers such as methylcellulose, nitrocellulose, ethylcellulose, methylhydroxypropylcellulose, hydroxyethylcellulose, cellulose sodium sulfate, hydroxypropylcellulose, sodium carboxymethylcellulose(CMC), crystalline cellulose, and cellulose powder; and alginic acid series polymers such as sodium alginate, and propylene glycol alginate.

Examples of synthetic polymers include silicone compounds such as a silicone resin forming a three-dimensional network structure and a silicone rubber; vinyl series polymers such as polyvinyl alcohol, polyvinyl methyl ether, polyvinylpyrrolidone and carboxyvinyl polymer(Carbopol); polyoxyethylene series polymers such as polyethylene glycol 2,000, 4,000, and 6,000; polyoxyethylene polyoxypropylene copolymers; acrylic series polymers such as sodium polyacrylate, polyethyl acrylate, and polyacrylamide; and polymers such as polyethyleneimine and cationic polymers.

Examples of inorganic water-soluble polymers include bentonite, aluminum magnesium silicate(Veegum), laponite, hectorite and anhydrous silicic acid.

Examples of thickeners include gum arabic, carrageenan, karaya gum, tragacanth gum, carob gum, quinceseed (*Cydonia oblonga*), caseine, dextrin, gelatin, sodium pectinate, sodium alginate, methylcellulose, ethylcellulose, CMC, hydroxyethylcellulose, hydroxypropylcellulose, PVA, PVM, PVP, sodium polyacrylate, carboxyvinyl polymer, locust bean gum, guar gum, tamarind gum, dialkyldimethylammonium sulfate cellulose, xanthan gum, aluminum magnesium silicate, bentonite and hectorite.

A cosmetic product form to which the invention can be applied is not limited particularly, and may for example be a fragrance product such as a perfume and a cologne; a body cosmetic product for a body oil; a sun-care body cosmetic product such as a sunscreen and after-sun lotion; an insect-repelling body cosmetic product such as an insect repeller and mosquito screen; a make-up cosmetic product; a skin or hair cleansing product; or a product for enamel remover.

A composition of the invention can be also applied preferably to a display article by virtue of its beautiful appearance and of the color development from its initial colorless appearance.

A color-developing composition of the invention which is stable over a time period is discussed below.

The color-developing composition discussed here is similar to a composition consisting of two discrete liquid phases described above with regard to the principle for the color development based on a very slight difference in the refractive index. The present composition develops a color to give a clear color by adjusting the difference in the refractive index between the liquid phase and the silica powder at a very slight difference. The color can further be changed by manipulating the difference in the refractive index.

Thus, assuming that the color of the external light observed through the inventive composition is of the transmitting light while the color of the entire composition except for the transmitting light is of the scattering light, when the liquid phase refractive index $n1$ and silica powder refractive index $n2$ are changed in such a manner that the value of $n1-n2$ is changed from a positive value to a negative value within the range specified by Equation (1) shown below, then the transmitting light and the scattering light undergo the change in color while almost keeping their complementary color relationship.

$$|n1-n2|<0.05 \tag{1}$$

In order to make this phenomenon more marked, Equation (1) is preferably the following equation:

$$|n1-n2|<0.02$$

and more preferably the following equation:

$$|n1-n2|<0.01.$$

The refractive index difference between a liquid phase and a silica powder can be adjusted precisely on the basis of the amount of the components of the liquid phases. It is also possible to change the color by changing the temperature of the composition.

A liquid phase employed in the inventive composition may be a non-polar substance or polar substance such as oils, fats and fatty oils, waxes, alcohols and water, which may be employed alone or in combination. When using water and alcohols, a water-soluble substance may be dissolved. When oils, fats and fatty oils, and waxes are employed then a component capable of being dissolved therein can be added.

In order to exert the effect of the invention markedly, it is preferable that transmittance of the white light through a liquid phase whose light path is 10 mm is 80% or higher.

It is also possible when using waxes or fats and fatty oils that the liquid phase is solidified into a gel or liquid crystal provided that the color development is not affected adversely, whereby providing a color-developing composition whose liquid phase is a transparent solid or semisolid. A composition whose liquid phase is a transparent solid or semisolid without affecting the color development adversely mentioned here means a composition which exhibits a transmittance (% T) at 550 nm of 20% T or higher, when measured by a spectrophotometer after it is filled in glass plates whose light path sandwiched by 1-mm thick glass plates is adjusted at 1 mm, cooled, solidified, and allowed to stand at 25° C. for 1 hour. Preferably the % T is 25% or higher, more preferably 30% or higher. A composition fulfilling this requirement can provide a transparent solid or semi-solid composition capable of developing a color.

When a powder having a high refractive index or low refractive index is employed as a solid phase, then it becomes difficult for the relationship with the refractive index of the liquid phase to fulfill the Equation (1) shown above, and for the purpose of exerting the effect of the invention the refractive index of the powder in the solid phase preferably fulfills: 1.30<n2<2.0 more preferably, 1.30<n2<1.60. Since a silica has a refractive index of about 1.45 to 1.50 and can fulfill Equation (1) when combined with a liquid component employed in cosmetic products such as oils, fats, waxes and alcohols in view of the refractive indexes of such components (1.30 to 1.55), it is preferable as a powder employed in the invention.

A spherical silica powder is known as a satisfactorily lubricant powder among the powders employed for the purpose of improving the usability, and its smoothness is a characteristic skin touch which has been utilized in cosmetic products for a long time. A dynamic frictional coefficient is employed frequently as a parameter indicative of the spreadability of a cosmetic powdery material. A spherical silica has a dynamic frictional coefficient as low as 0.28, which is comparable with that of a talc (0.28 to 0.30) known as a satisfactorily spreadable powder, and is also a highly lubricating powder because of the value lower than that of a spherical nylon employed as a skin touch-improving agent (0.33). Also since it is an inorganic powder, it has an excellent solvent resistance and can be combined with various bases. The surface of the silica powder can be treated provided that the characteristics are not changed substantially.

The morphology of a silica powder employed in the inventive composition is preferably spherical since its color development mechanism is resulting from the interface between a solid phase and a liquid phase and the highest effect is observed when the color development mechanism is effected at a uniform continuous boundary. Accordingly, while the most preferable morphology is a true sphere, a spherical morphology is also preferable and the true sphere is not always necessary since a continuous surface may allow the function to be exerted generally, and a non-sphere, i.e., a edged or amorphous(shapeless) powder may also serve to exert the function sufficiently, although the function becomes weaker when compared with a spherical powder.

The particle size of a silica is preferably 0.1 to 200 μm, more preferably 0.5 to 100 μm, particularly 1 to 50 μm, in view of the effectiveness of the inventive composition and the skin touch of the composition. Thus, an extremely small particle size leads to an insufficient color development, while a larger particle size leads to a difficulty in exhibiting a shining color due to the effect of the scattering and reflecting lights and is also undesirable in a cosmetic composition from the viewpoint of the skin touch since a larger particle leads to roughness and harshness.

The amount of a silica powder to be added is 0.01 to 60% by mass based on the entire composition, in view of the effectiveness of the inventive composition and the skin touch of the composition. A smaller amount leads to an insufficient development of a shining color, while a larger amount leads to a turbidness of the entire composition, resulting in a difficulty in developing a shining color. More preferably, the amount to be added is 0.1 to 40% by mass, especially 1 to 10% by mass.

The oil employed in the liquid phase of the inventive composition is not limited particularly as long as it is a liquid oil generally used in cosmetics. Examples of such oils include silicone oils such as chain polysiloxanes(e.g., dimethylpolysiloxane, methylphenyl polysiloxane, methylhydrogenpolysiloxane and the like) and cyclic polysiloxanes (e.g., hexamethylcyclotrisiloxane, decamethylcyclopentasiloxane, dodecamethylcycloheptasiloxane, tetramethyltetrahydrogencyclotetrasiloxane and the like); and hydrocarbons represented by isoparaffin series hydrocarbons.

Also, as an oil component such as fats and fatty oils, waxes and other oil components employed in the liquid phase of the inventive composition, various liquid fats and fatty oils, solid fats and fatty oils, and waxes mentioned in the explanation of the liquid-liquid color-developing composition of the invention as well as hydrocarbon oils such as liquid paraffin, ozocerite, squalene, pristane, paraffin, ceresin, squalene, vaseline, and microcrystalline wax can be used together with the liquid oil described above for the liquid phase.

Further, various higher fatty acids, higher alcohols and ester oils mentioned in the explanation of the liquid-liquid color-developing composition of the present invention can be contained in the liquid phase of the inventive composition.

When the oil described above is solid at a normal temperature, it may be heated and dissolved to be used.

Among the oils mentioned above, it is particularly preferable that a hydrocarbon oil or a silicone oil is selected to be used, in view of the effectiveness of the inventive composition.

In addition to the components mentioned above, the other components generally used in cosmetics can be added to the inventive composition as long as the effect of the invention is not spoiled, if necessary. Examples thereof include silicone compounds such as a silicone resin forming a three-dimensional network structure and a silicone rubber; and moisturizing agents and ultraviolet absorbers mentioned in the explanation of the liquid-liquid color-developing composition of the present invention.

Also, for the purpose of thickening or the like, as long as the effect of the present invention is not spoiled(e.g., as long as a disadvantage due to excess addition is not demonstrated), various natural polymers, semi-synthetic polymers, synthetic polymers, inorganic water-soluble polymers and thickeners mentioned in the explanation of the liquid-liquid color-developing composition of the present invention can be added to the composition.

Further, for the purpose of the effect of the invention and more attractive appearance of the composition, powders normally used in cosmetics or the other powders can be used as long as the original function of the invention is not spoiled. Examples thereof include inorganic powders such as kaolin, sericite, talc, magnesium carbonate, calcium carbonate, diatomaceous earth, magnesium silicate, calcium silicate, aluminum silicate, barium silicate, barium sulfate, strontium silicate, tungsten acid metal salt, hydroxyapatite, zeolite, boron nitride, ceramic powder, muscovite, phlogopite, red mica, biotite, synthetic mica, lithia mica, vermiculite, titanium oxide, barium titanate, cerium oxide, zirconium oxide, bismuth oxychloride, zinc oxide, stannic oxide, aluminum oxide, magnesium oxide, barium sulfate, calcium fluoride, and magnesium fluoride; organic polymer powders inorganic powders such as polyamide resin powder (e.g., nylon powder), polyethylene powder, polystyrene powder, urethane resin powder, benzoguanamine powder, polyethylene tetrafluoride powder, distyrenebenzene polymer powder, epoxy polymers, polyacryl polymers, methyl polymathacrylate polymers, resin powder of copolymer of styrene and acrylic acid, silicone powder, and microcrystalline cellulose powder; and pearl luster materials or glitters such as metallic foils, plastic laminate powders, metallized resin powders, and resin-coated metallic foils.

Also, for the purpose of coloring and the like, powders can be used as long as the effect of the present invention is not spoiled (e.g., as long as a disadvantage due to excess addition is not demonstrated). Examples thereof include organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; zirconium, barium or aluminum lake organic pigments such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1; and natural colors such as chlorophyll, and β-carotene.

Furthermore, when the present composition is used as a cosmetics preparation, sugars, amino acids, pH adjusting agents, sequestering agents, antioxidants, perfumes, antiseptics, anti-inflammatory agents, whitening agents, extracts from animals or plants, skin activators, blood circulation accelerators, antiseborrheic drugs, and the other drugs can be used, if necessary.

A cosmetic product form to which the invention can be applied may for example be a skin-care product such as a lotion, a milky lotion and a cream; a body cosmetic preparation for a cleansing/or bath such as a body shampoo and a scrub cleansing preparation; a body cosmetic preparation for treatment such as a milky lotion and a cream; a fragrance cosmetic preparation such as a powder and a cologne; a sun-care body cosmetic preparation such as a sunscreen and after-sun lotion; an insect-repelling body cosmetic preparation such as an insect repeller and mosquito screen; a make-up cosmetic preparation; a skin or hair cleansing product; or a product for enamel remover, which can be applied all over the body including face.

A cosmetic formulation to which the invention can be applied may be selected appropriately according to the product form desired as exemplified above and is not limited particularly. For example, an ointment, a cream, a milky lotion, a lotion, a powder-dispersed cosmetic preparation or the like can be selected.

A composition of the invention can be also applied preferably to a display article by virtue of its beautiful appearance.

In the following, although the invention will be further explained by using embodiments, it is not limited thereto. The parts to be added is shown by weight % with respect to the whole object.

<Liquid-liquid Color-Developing Composition>

EXAMPLE 1

42.8 parts of decamethylcyclopentasiloxane and 21.2 parts of phenylmethyl polysiloxane were mixed. 11.1 parts of ion exchange water and 24.9 parts of glycerin were then mixed to obtain an aqueous phase. The both mixtures were combined to obtain a liquid mixture whose transmitting light was of a yellowish green and those circumferential light was of a reddish purple. When this liquid was allowed to stand for a while, it was separated into transparent 2 phases, which underwent the color development when mixed again.

Figure 2:
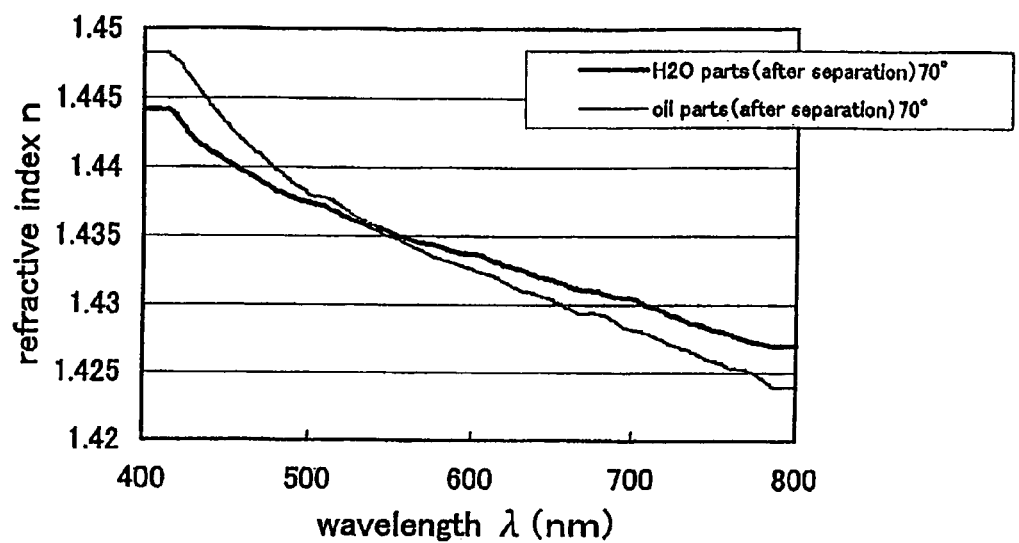
FIG. 2 shows a graph indicating a wavelength dependency, when measured by an ellipsometer, of refractive indexes of an aqueous phase and an oil phase as constituents of a color-developing composition according to one embodiment of the invention.

The wavelength dependency of the refractive index of the aqueous phase and the oil phase thus separated was determined using an ellipsometer. The results are shown in FIG. 2. Both of the aqueous phase and the oil phase exhibited the change in the refractive index by the wavelength, and the refractive index tended to be lower at a higher wavelength. While these two lines gave their crossing point at 540 nm, which means that at 540 nm there is no difference in the refractive index between the aqueous phase and the oil phase and the light having this wavelength can transmit without scattering even in the mixture of the aqueous phase and the oil phase.

On the other hand, there was a difference in the refractive index between the aqueous phase and the oil phase at the wavelengths other than 540 nm, and the light of such other wavelengths causes the scattering. Accordingly, the reddish purple color which is the complementary color of the 540 nm yellowish green is of the scattering light. The transmitting light is observed as the yellowish green color and the circumferential light is observed as the reddish purple color when this formulation is shaken vigorously to disperse the two phases, and this phenomenon can be explained based on the findings obtained using the ellipsometer.

EXAMPLE 2

Figure 3:
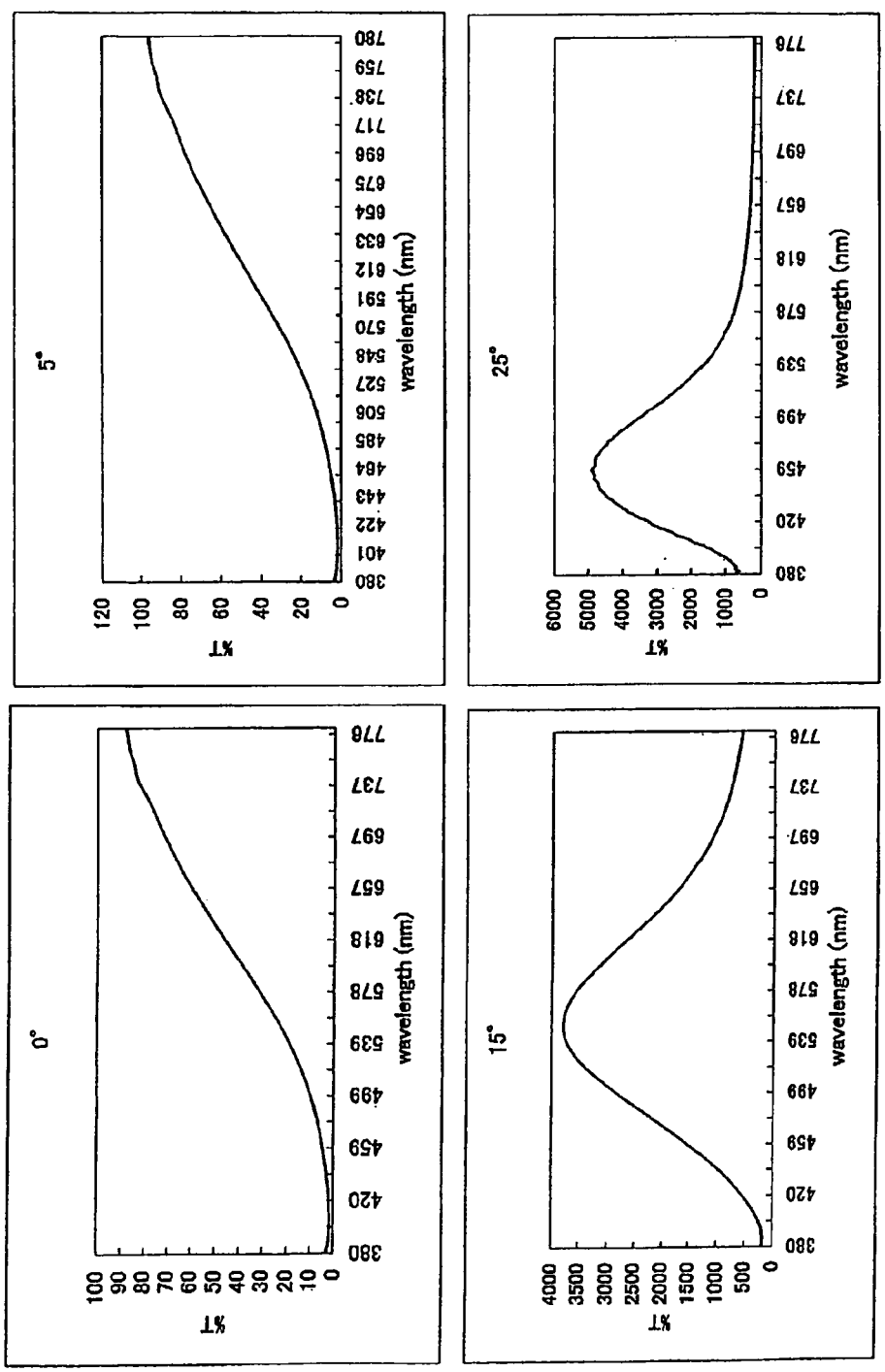
FIG. 3 shows a spectrum of a measured light intensity at 380 nm to 780 nm, when an angle at which the dispersion obtained by mixing and dispersing a color-developing composition according to one embodiment of the invention receives the white light irradiated in a certain direction is varied.

37.3 parts of decamethylcyclopentasiloxane, 12.2 parts of phenylmethylpolysiloxane and 7.0 parts of perfumes were mixed. The refractive index of the oil phase thus obtained was 1.4320. Then 13.2 parts of ion exchange water and 30.8 parts of glycerin were mixed to obtain an aqueous phase. Its refractive index was 1.4310. The oil phase and the aqueous phase were mixed to obtain a composition whose transmitting light was orange and whose scattering light was bluish green. The spectrum of the observed light intensity at 380 nm to 780 nm with varying the angle at which the light is received is shown in FIG. 3. A broad peak was observed at 0 and 5° in the range from yellow to red, allowing the overall color to appear as an orange color, which is observed as a transmitting light. On the other hand, colors which peaked at 540 nm and 460 nm, respectively, were observed at 15° and 25°, and corresponded to the scattering light color, which changed from green to blue depending on the observation angle. This composition was separated again into two phases after 5 minutes to become colorless, but then developed the color by mixing and dispersing again. This composition gave the aroma off satisfactorily, and was not sticky in spite of a non-alcohol fragrance.

EXAMPLE 3

Figure 4:
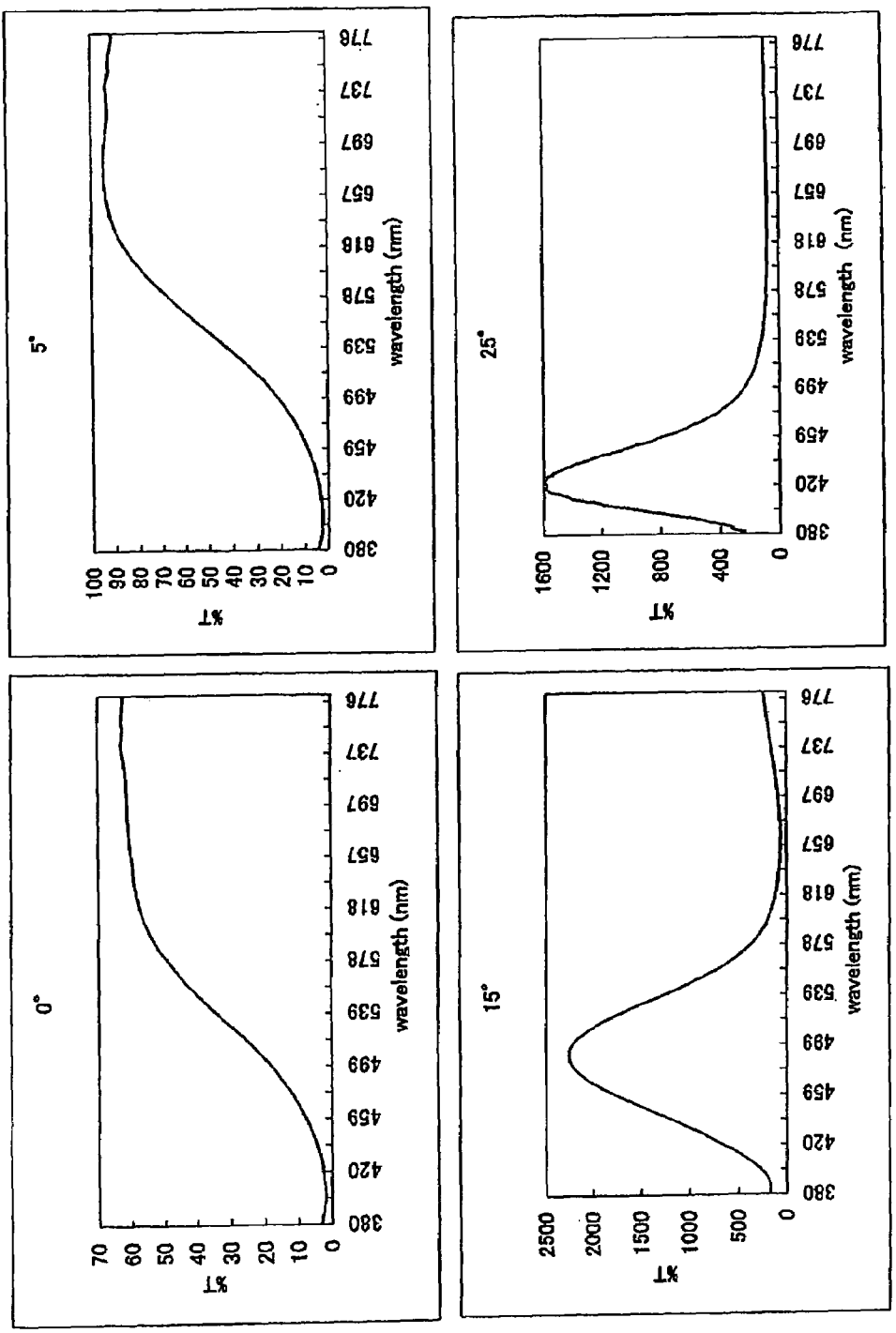
FIG. 4 shows a spectrum of a measured light intensity at 380 nm to 780 nm, when an angle at which the dispersion obtained by mixing and dispersing a color-developing composition according to one embodiment of the invention receives the white light irradiated in a certain direction is varied.

A mixture of 12.9 parts of ion exchange water and 31.1 parts of glycerin (refractive index: 1.4319) was combined and mixed with the oil phase in Example 2 to obtain a composition whose transmitting light was yellow and whose scattering light was blue. The angle dependency of these colors are shown in FIG. 4. At 0° and 5°, the peak was shifted to shorter wavelengths as compared with Example 1, and the orange color was changed into a yellow color. Also at 15° and 25°, the shift to further shorter wavelengths than Example 2 gave the wavelengths of 490 nm and 420 nm, resulting in a purple color from blue. The physical characteristics other than the color were similar to those in Example 2.

EXAMPLE 4

Figure 5:
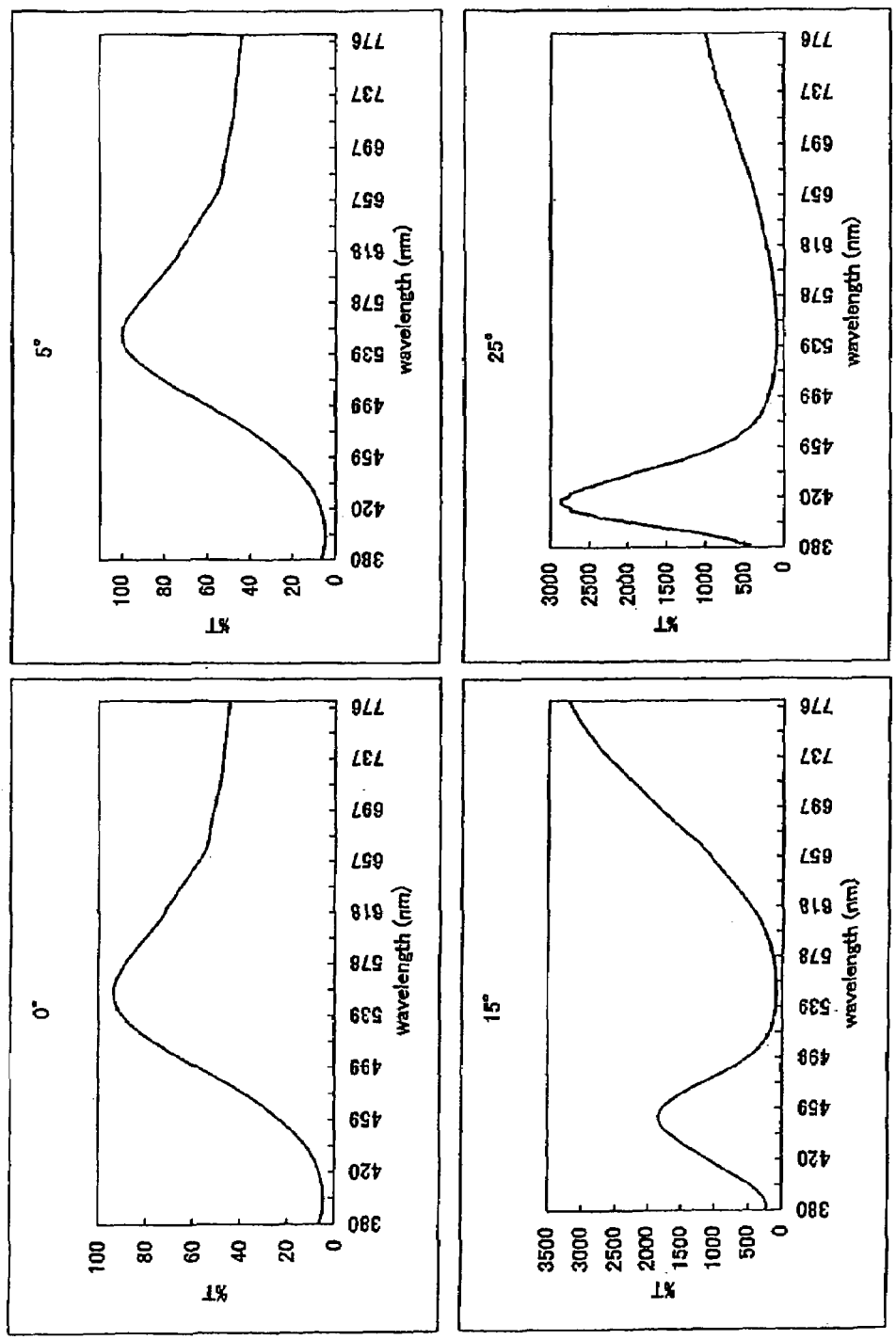
FIG. 5 shows a spectrum of a measured light intensity at 380 nm to 780 nm, when an angle at which the dispersion obtained by mixing and dispersing a color-developing composition according to one embodiment of the invention receives the white light irradiated in a certain direction is varied.

A mixture of 12.5 parts of ion exchange water and 31.5 parts of glycerin (refractive index: 1.4332) was combined and mixed with the oil phase in Example 2 to obtain a composition whose transmitting light was yellowish green and whose scattering light was purple. The angle dependency of these colors are shown in FIG. 5. At 0° and 5°, the peak was shifted to further shorter wavelengths as compared with Example 3, and the yellow color was changed into a green color. Also at 15° and 25°, the shift to further shorter wavelengths than Example 3 gave the wavelengths of 450 nm and 420 nm, resulting in a purple color. A red color peak was newly observed, resulting in a color close to a reddish purple. The physical characteristics other than the color were similar to those in Example 2.

EXAMPLE 5

Figure 6:
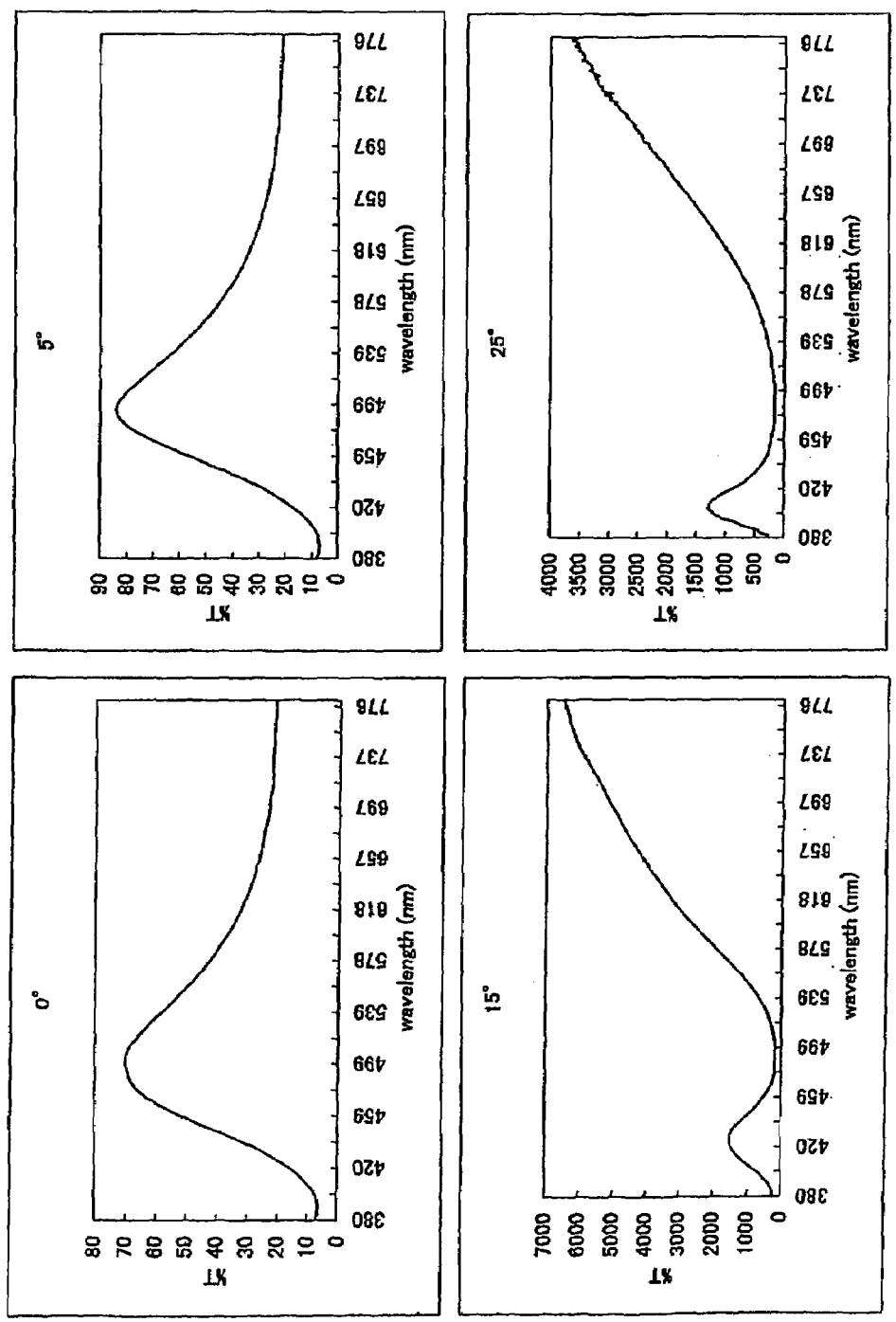
FIG. 6 shows a spectrum of a measured light intensity at 380 nm to 780 nm, when an angle at which the dispersion obtained by mixing and dispersing a color-developing composition according to one embodiment of the invention receives the white light irradiated in a certain direction is varied.

A mixture of 12.2 parts of ion exchange water and 31.8 parts of glycerin (refractive index: 1.4341) was combined and mixed with the oil phase in Example 2 to obtain a composition whose transmitting light was bluish green and whose scattering light was orange. The angle dependency of these colors are shown in FIG. 6. At 0° and 5°, the peak was shifted to further shorter wavelengths as compared with Example 3, and the green color was changed into a blue color. Also at 15° and 25°, although the shift to further shorter wavelengths than Example 4 was observed, the peak was small. Another peak in the range of red or orange was observed. The physical characteristics other than the color were similar to those in Example 2.

EXAMPLE 6

Figure 7:
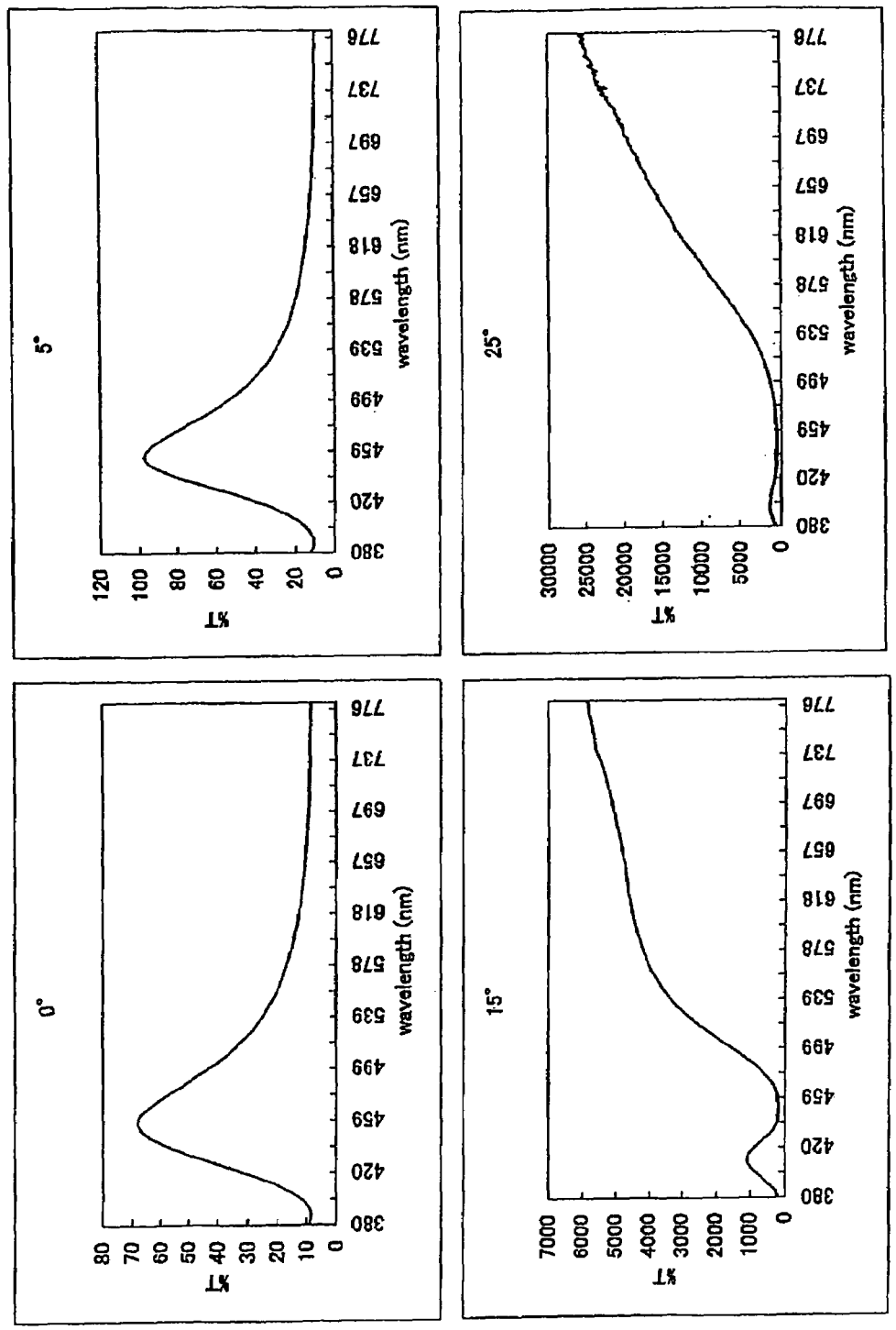
FIG. 7 shows a spectrum of a measured light intensity at 380 nm to 780 nm, when an angle at which the dispersion obtained by mixing and dispersing a color-developing composition according to one embodiment of the invention receives the white light irradiated in a certain direction is varied.

A mixture of 11.9 parts of ion exchange water and 32.1 parts of glycerin (refractive index: 1.4351) was combined and mixed with the oil phase in Example 2 to obtain a composition whose transmitting light was purple and whose scattering light was yellow. The angle dependency of these colors are shown in FIG. 7. At 0° and 5°, the peak was shifted to further shorter wavelengths as compared with Example 6, and the blue color at 450 nm was changed into a purple color. Also at 15° and 25°, a peak in the range from orange to yellow was observed. The physical characteristics other than the color were similar to those in Example 2.

<Silica-Dispersing Color-Developing Composition>

1. Color Development and Transparency of Inventive Composition

When 25 ml of a composition containing a spherical silica as a solid phase and a polysiloxane as a liquid phase as shown in TABLE 1 below, whose difference in the refractive index between its solid phase and liquid phase was 0.002 was placed in a 50-ml transparent cylindrical container and examined for its appearance visually, it exhibited a color development and had an excellent transparency. In this color development, the transmitting light when the composition was held up to an external light was green, otherwise being observed as a purple color.

Figure 8:
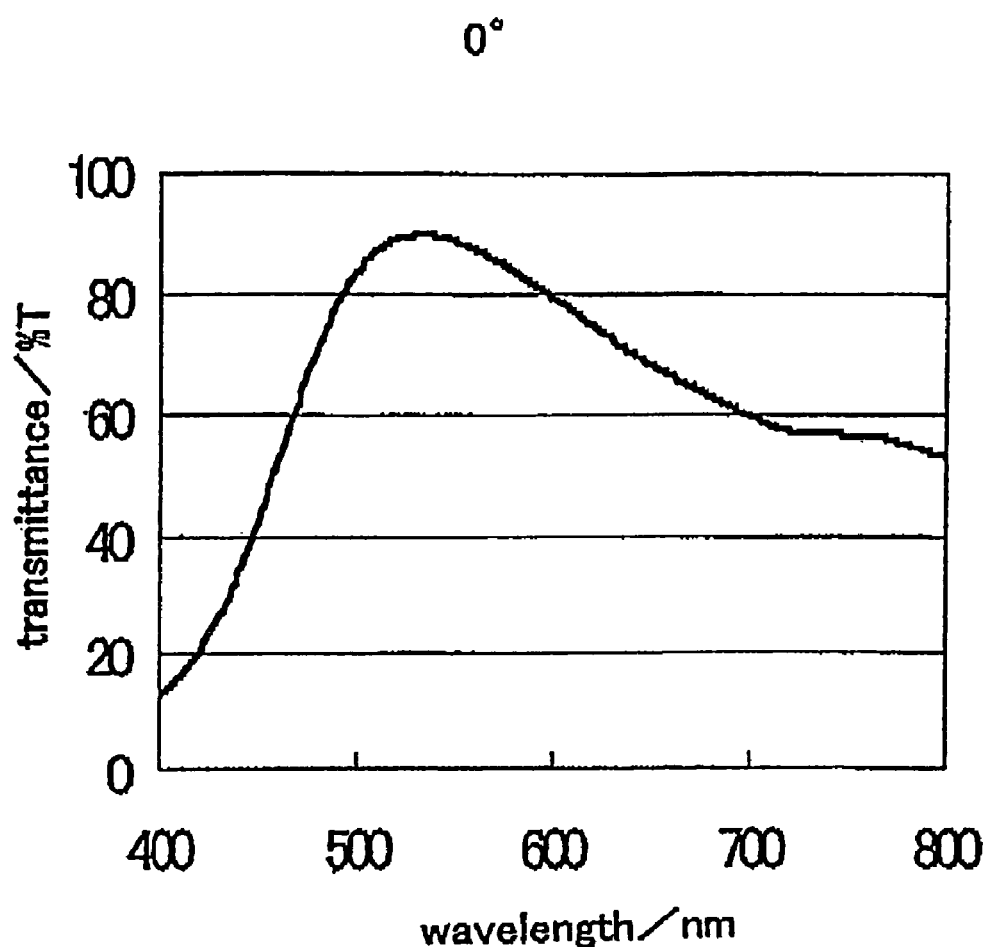
FIG. 8 shows a spectrum of a measured light intensity at 400 nm to 800 nm when an angle at which a color-developing composition according to one embodiment of the invention receives the white light irradiated in a certain direction is 0°.
Figure 9:
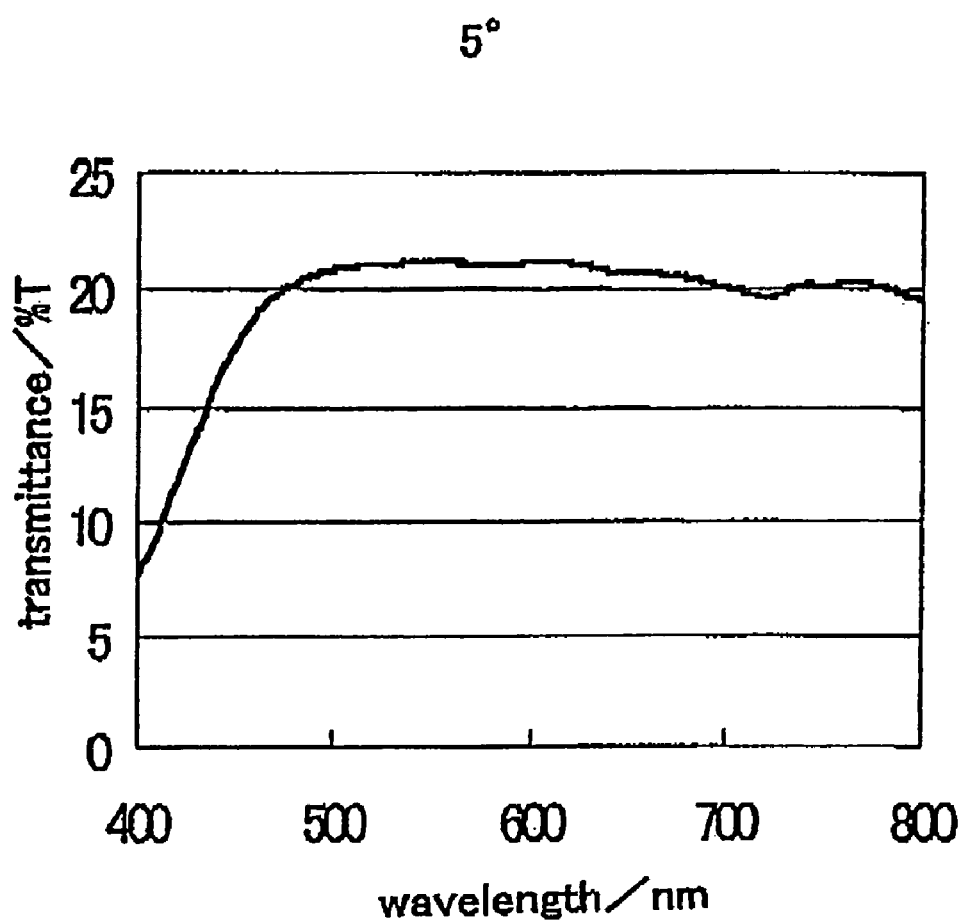
FIG. 9 shows a spectrum of a measured light intensity at 400 nm to 800 nm when an angle at which a color-developing composition according to one embodiment of the invention receives the white light irradiated in a certain direction is 5°.
Figure 10:
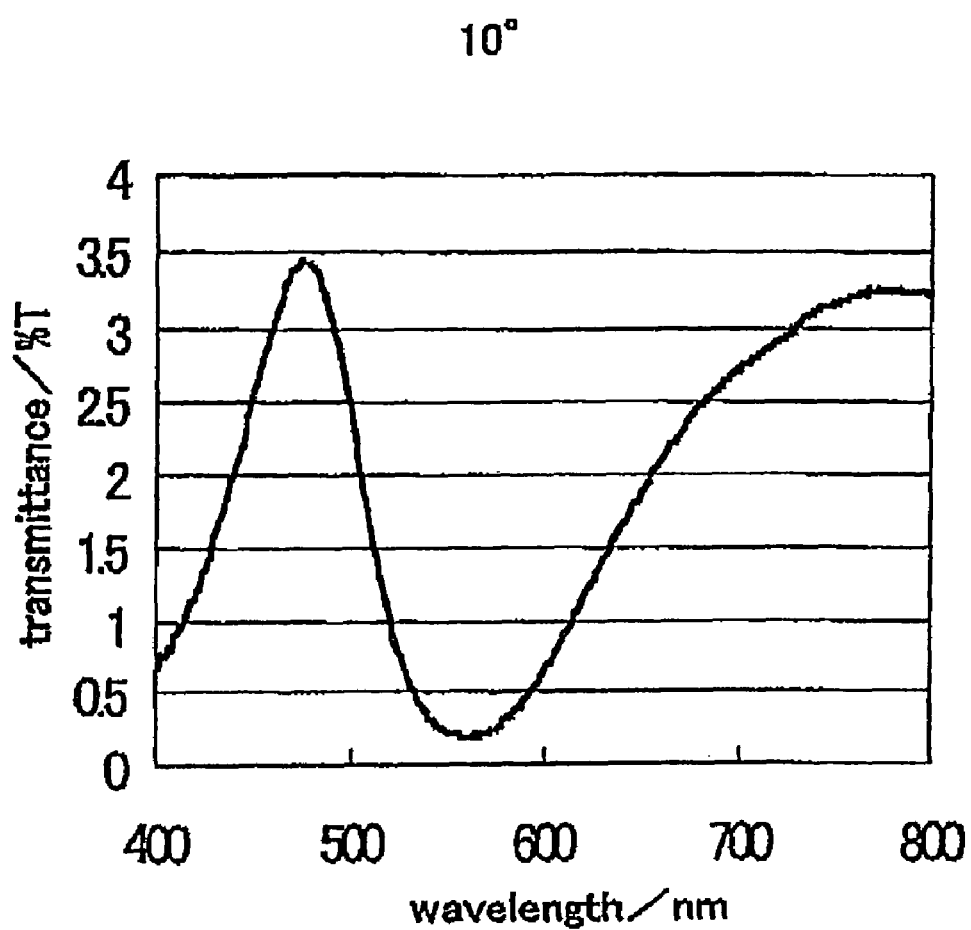
FIG. 10 shows a spectrum of a measured light intensity at 400 nm to 800 nm when an angle at which a color-developing composition according to one embodiment of the invention receives the white light irradiated in a certain direction is 10°.
Figure 11:
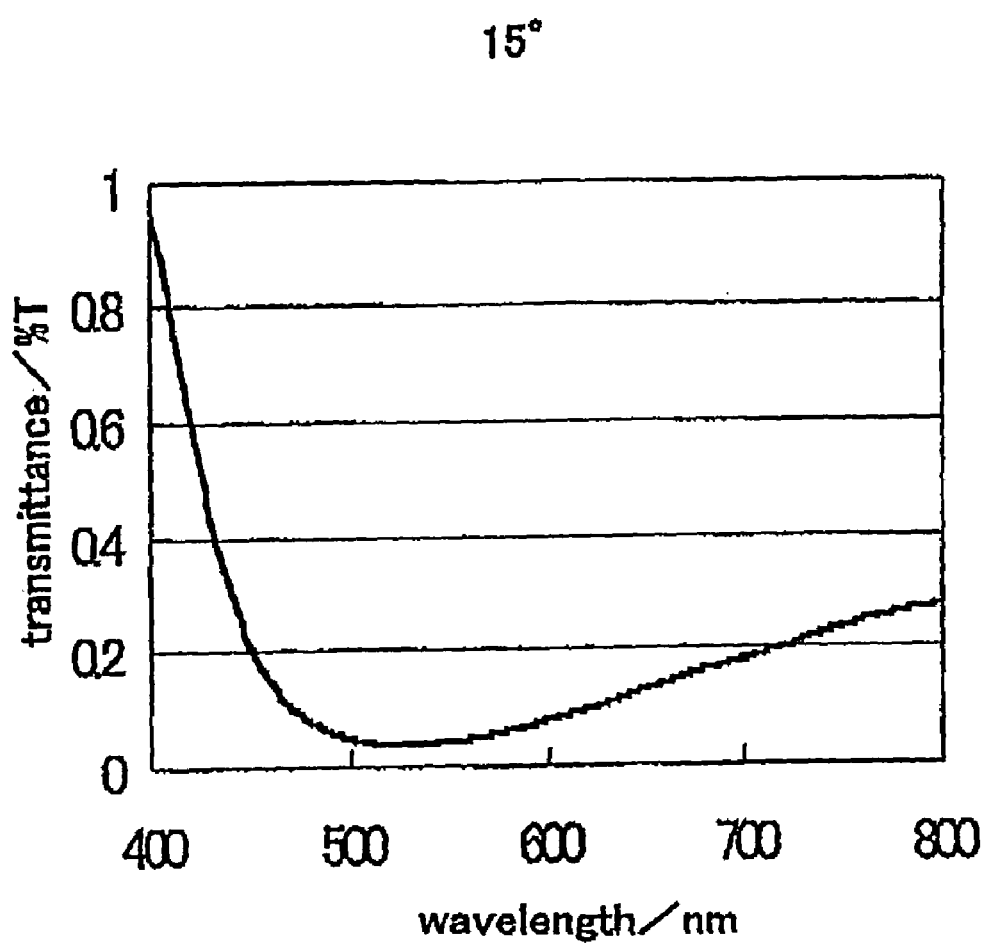
FIG. 11 shows a spectrum of a measured light intensity at 400 nm to 800 nm when an angle at which a color-developing composition according to one embodiment of the invention receives the white light irradiated in a certain direction is 15°.
Figure 12:
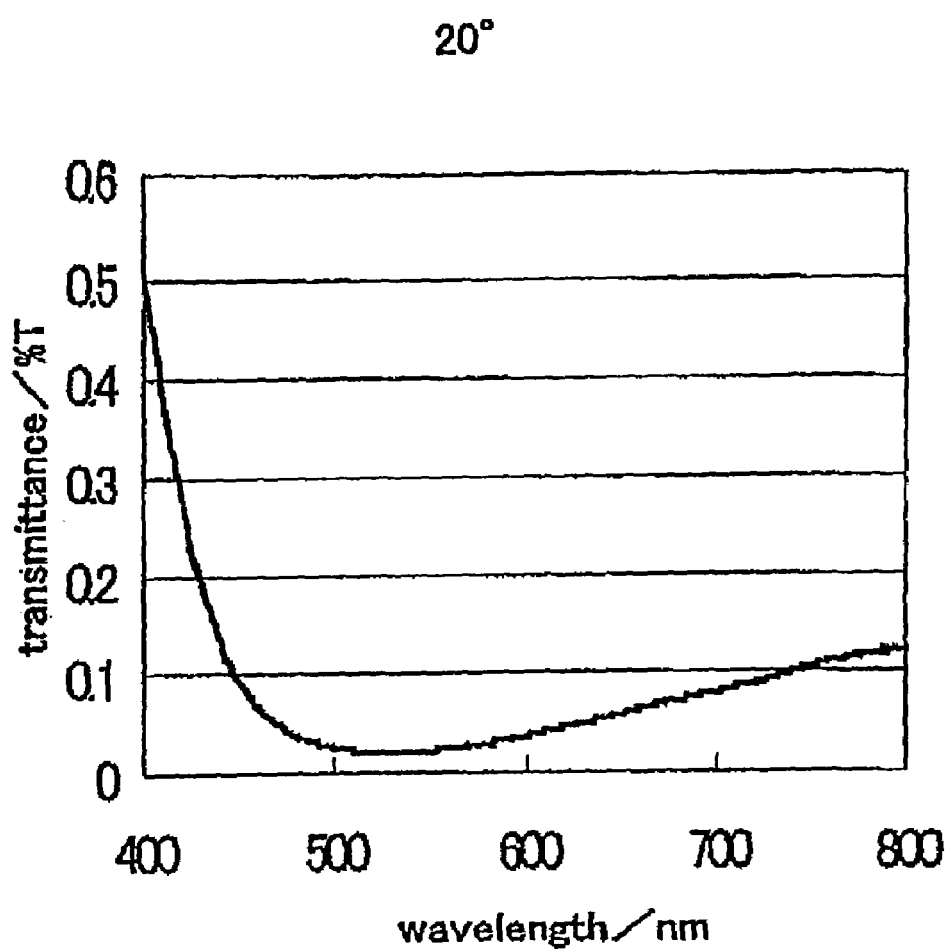
FIG. 12 shows a spectrum of a measured light intensity at 400 nm to 800 nm when an angle at which a color-developing composition according to one embodiment of the invention receives the white light irradiated in a certain direction is 20°.
Figure 13:
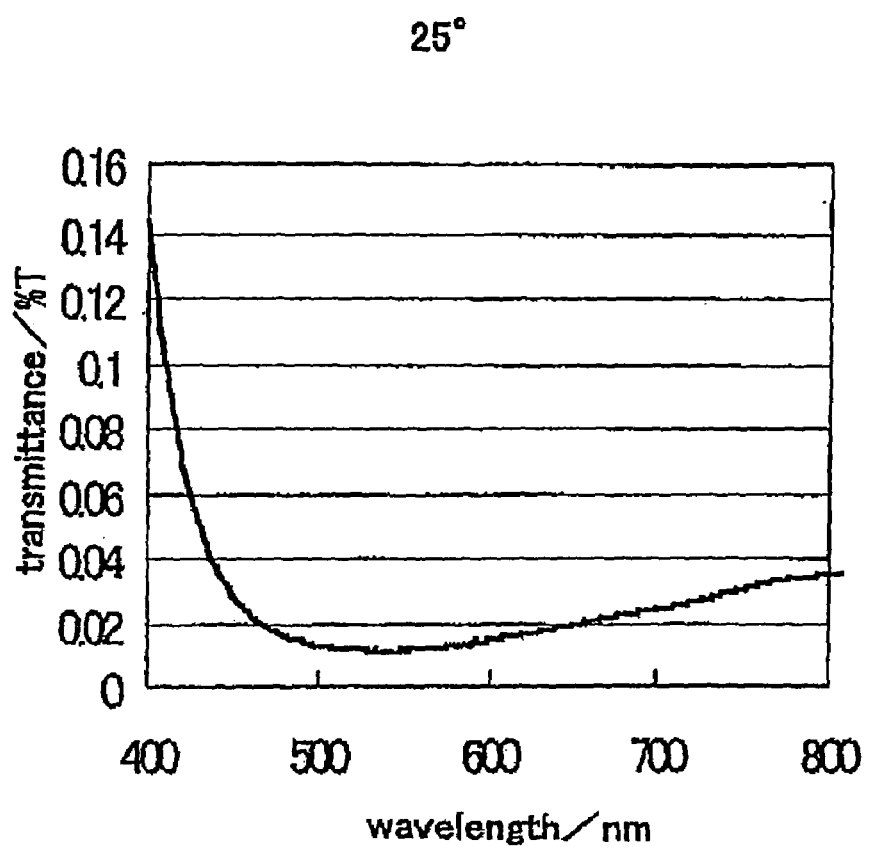
FIG. 13 shows a spectrum of a measured light intensity at 400 nm to 800 nm when an angle at which a color-developing composition according to one embodiment of the invention receives the white light irradiated in a certain direction is 25°.
Figure 14:
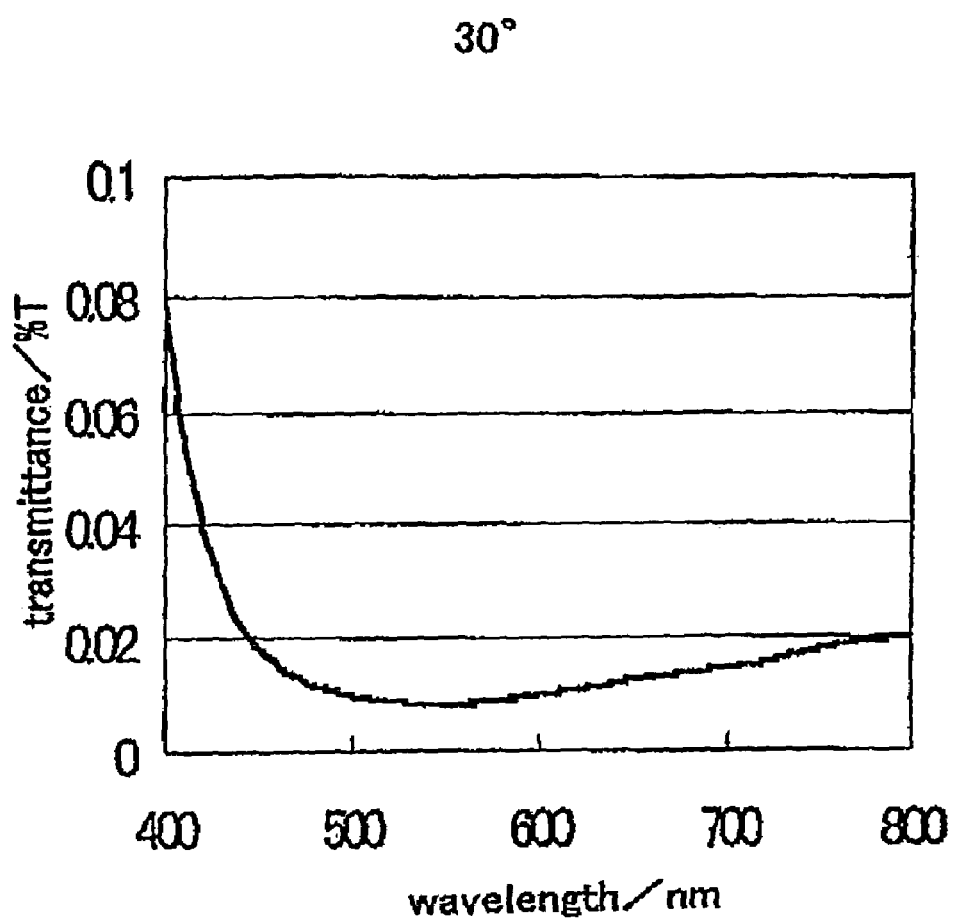
FIG. 14 shows a spectrum of a measured light intensity at 400 nm to 800 nm when an angle at which a color-developing composition according to one embodiment of the invention receives the white light irradiated in a certain direction is 30°.
Figure 15:
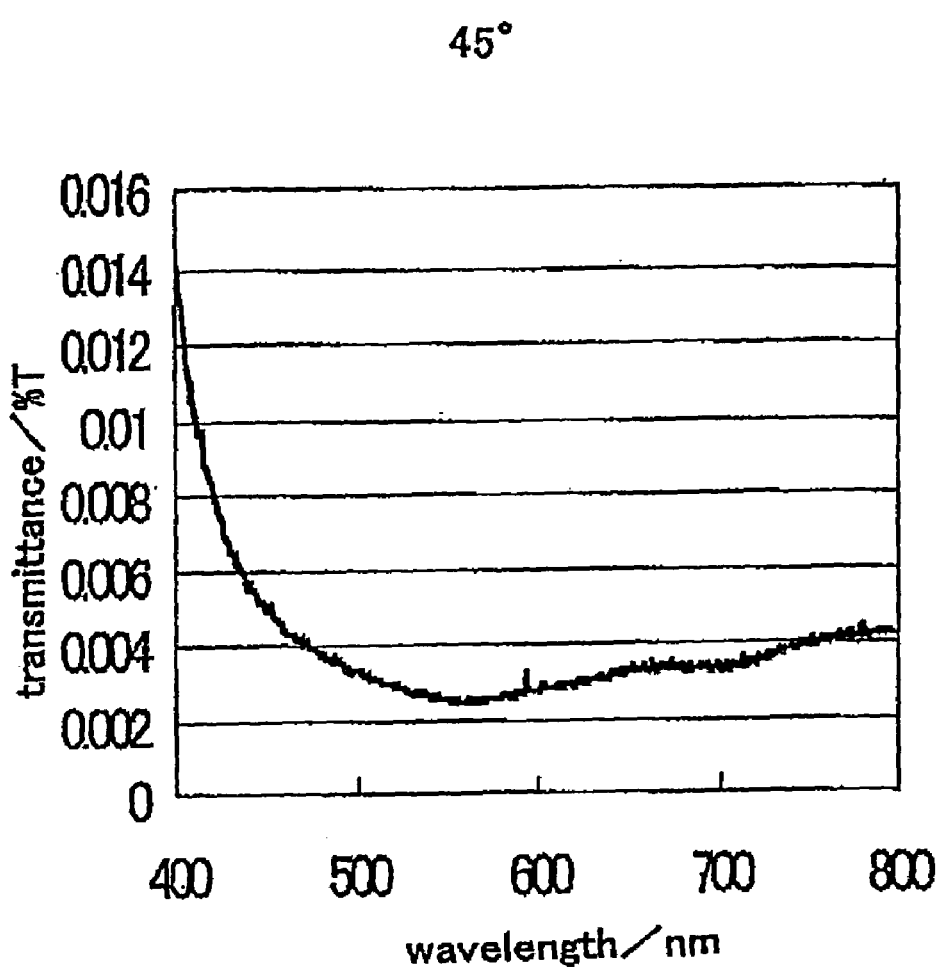
FIG. 15 shows a spectrum of a measured light intensity at 400 nm to 800 nm when an angle at which a color-developing composition according to one embodiment of the invention receives the white light irradiated in a certain direction is 45°.

Then this composition was placed in a cell whose light path was 10 mm and was examined for the spectrum of the observed light intensity over the range from 400 to 800 nm using a spectrophotometer with varying the angle at which the composition received the white light irradiated in a certain direction. The spectrum when the angle was 0°, i.e., that of the transmitting light, is shown in FIG. 8. The peak wavelength λmax of this spectrum was 530 nm, which corresponded to the green color observed when the transmitting light was evaluated visually. The transmittance (% T) at the peak wavelength λmax was as high as 90%.

FIGS. 9 to 15 show the spectra of the observed lights measured with changing the angle from 5° to 45°. A large angle resulted in a lower peak of the transmitting light spectrum, and the transmittance became lower even within the peak wavelength region of the transmitting light spectrum when the angle reached 10°, at a larger angle than which the peak was no longer observed in the transmitting light spectrum. This phenomenon is in agreement with the fact that scattering light is the complementary color of the transmitting light on the visual basis.

TABLE 1

| Component | Experiment 1 |
| --- | --- |
| Spherical silica (*1) | 5.0 |
| Cyclopolysiloxane | 3.0 |
| Dimethylpolysiloxane | Balance(to 100 wt %) |
| Refractive index of silica | 1.48 |
| Refractive index of liquid phase | 1.482 |

(*1) "P-1500" manufactured by CATALYSTS&CHEMICALS IND. CO., LTD.

2. Difference in Refractive Index Between Liquid Phase and Silica and Color Development of Composition A silica powder and a liquid phase whose refractive index was adjusted by using two types of polysiloxane were mixed simply to obtain the samples shown in Tables 2 to 4. Each sample was examined for its wavelength λmax at which its transmittance became the highest and also for such a transmittance based on the transmission spectrum, and the color of the transmitting light was judged organoleptically, and then it was also examined for the color development intensity and the transparency. The results are shown in Tables 5 and 6.

(1) Color Development Intensity Evaluation

Each sample was shaken, and a 20 to 25 ml aliquot was placed in a transparent cylindrical container and stirred. Then 12 male and 10 female panelists (22 in total) visually evaluated the color development intensity, which was judged according to the criteria shown below on the basis of the number of the panelists who felt that the color was intense.

<Evaluation Criteria>
□: 20 or more panelists felt that it developed a color.
○: 10 or more and less then 20 panelists felt that it developed a color.
□: 1 or more and less then 10 panelists felt that it developed a color.
×: None panelists felt that it developed a color.

(2) Transparency Evaluation

Each sample was shaken, and a 20 to 25 ml aliquot was placed in a transparent cylindrical container and stirred. Then 12 male and 10 female panelists (22 in total) visually evaluated the transparency, which was judged according to the criteria shown below on the basis of the number of the panelists who felt that the sample was transparent.

<Evaluation Criteria>
□: 20 or more panelists felt that it was transparent.
○: 10 or more and less then 20 panelists felt that it was transparent.
□: 1 or more and less then 10 panelists felt that it was transparent.
×: None panelists felt that it was transparent.

TABLE 2

| Component | Exp. 2 | Exp. 3 | Exp. 4 |
|---|---|---|---|
| Spherical silica | 2.0 | 2.0 | 2.0 |
| Cyclopolysiloxane | 38.0 | 35.0 | 30.0 |
| Dimethylpolysiloxane | Balance | Balance | Balance |
| Refractive index of silica | 1.48 | 1.48 | 1.48 |
| Refractive index of liquid phase | 1.471 | 1.475 | 1.479 |
| Refractive index difference between silica and liquid phase | 0.009 | 0.005 | 0.001 |

TABLE 3

| Component | Exp. 5 | Exp. 6 | Exp. 7 |
|---|---|---|---|
| Spherical silica powder | 2.0 | 2.0 | 2.0 |
| Cyclopolysiloxane | 28.0 | 22.0 | 18.0 |
| Dimethylpolysiloxane | Balance | Balance | Balance |
| Refractive index of silica | 1.48 | 1.48 | 1.48 |
| Refractive index of liquid phase | 1.485 | 1.487 | 1.490 |
| Refractive index difference between silica and liquid phase | 0.005 | 0.007 | 0.010 |

TABLE 4

| Component | Exp. 8 | Exp. 9 | Exp. 10 |
|---|---|---|---|
| Spherical silica powder | 2.0 | 2.0 | 2.0 |
| Cyclopolysiloxane | — | 50.0 | — |
| Dimethylpolysiloxane | Balance | Balance | — |
| Methylphenylpolysiloxane | — | — | Balance |
| Refractive index of silica | 1.48 | 1.48 | 1.48 |
| Refractive index of liquid phase | 1.501 | 1.429 | 1.551 |
| Refractive index difference between silica and liquid phase | 0.021 | 0.051 | 0.071 |

TABLE 5

| Evaluation Item | Exp. 2 | Exp. 3 | Exp. 4 | Exp. 5 | Exp. 6 |
|---|---|---|---|---|---|
| Transmittance (% T) | 64 | 69 | 88 | 82 | 76 |
| λmax(nm) | 424 | 475 | 515 | 560 | 594 |
| Transmitting color | purple | blue | green | yellowish green | orange |
| Color-developing intensity | ○ | □ | □ | □ | ○ |
| Transparency | ○ | ○ | □ | ○ | □ |

TABLE 6

| Evaluation Item | Exp. 7 | Exp. 8 | Exp. 9 | Exp. 10 |
|---|---|---|---|---|
| Transmittance(% T) | 68 | 55 | 27 | 20 |
| λmax(nm) | 688 | 768 | — | — |
| Transmitting color | red | red | — | — |
| Color-developing intensity | □ | □ | x | x |
| Transparency | □ | □ | x | x |

As evident from Tables 5 and 6, each of Experiments 2 to 8 whose absolute value of the difference in the refractive index between the silica powder and the liquid phase did not exceed 0.05 exhibited the transmitting color corresponding to the difference in the refractive index and exhibited the transparency.

On the other hand, each of Experiments 9 and 10 whose absolute value of the difference in the refractive index between the silica powder and the liquid phase exceeded 0.05 gave a white-turbid composition, which was opaque and did not develop a color.

Among Experiments 2 to 8 exhibiting the color development and the transparency, each of Experiments 2 to 6 whose absolute value of the difference in the refractive index between the silica powder and the liquid phase did not exceed 0.01 exhibited a more marked color development, and a lower absolute value of the difference in the refractive index gave a higher intensity of the color development as well as a higher transparency.

3. Types of Powders and Skin Touch

Each sample of the formulations shown in Table 7 employing different types of the powders was prepared and applied on a skin to evaluate the skin touch. 20 well-trained panelists applied each sample to their skin and evaluated the skin touch organoleptically on the basis of the smoothness due to the spreading performance. Using the score by the panelist who felt a satisfactory skin touch as a standard, the sample was judged as any of the five degrees: Very good (5 points), Good (4 points), Moderate (3 points), Slightly poor (2 points) and Poor (1 point). The mean of the scores by 20 panelists was calculated and the skin touch was judged according to the following evaluation criteria. The results are shown in Table 7.

<Evaluation Criteria>
Mean of Scores
☐: 4.0 or more and 5.0 or less.
○: 3.0 or more and less then 4.0.
☐: 2.0 or more and less then 3.0.
×: 1.0 or more and less then 2.0.

TABLE 7

| Component | Exp. 11 | Exp. 12 | Exp. 13 | Exp. 14 |
|---|---|---|---|---|
| Spherical silica | 5.0 | | | |
| Spherical PMMA powder (*1) | | 5.0 | | |
| Spherical nylon powder (*2) | | | 5.0 | |
| Spherical silicone rubber powder (*3) | | | | 5.0 |
| Cyclopolysiloxane | 30.0 | 30.0 | 30.0 | 30.0 |
| Methylphenylpolysiloxane | Balance | Balance | Balance | Balance |
| Evaluation | ☐ | x | ☐ | ○ |

(*1) particle size: 6–8 μm.
(*2) nylon-12(particle size: 2–10 μm).
(*3) (dimethicone/vinyldimethicone)crosspolymer(particle size: 4.5–5.5 μm).

As evident from Table 7, the use of silica as a powder (Experiment 11) gave an excellent skin touch when compared with Experiments 12 to 14 which employed other powders. Accordingly, by using an inventive composition as a cosmetic preparation, smoothness due to the spreading performance specific to the silica can be provided.

4. Powder Morphology and Color Development and Transparency of Composition

Each of the samples having the formulations shown in Table 8 was prepared and examined for the relationship of the silica powder morphology with the color development and transparency of the composition. The morphology of the silica powder employed were spherical (Experiment 15) and amorphous(shapeless) (Experiment 16).

The color development intensity and the transparency of each sample were evaluated visually by the panelists based on the criteria similar to that described above. For evaluating the transmittance, each composition was filled in glass plates whose light path sandwiched by 1-mm thick glass plates was adjusted at 1 mm, cooled, solidified, allowed to stand at 25° C. for 1 hour, and examined for the transmittance (% T) at 550 nm by a spectrophotometer, which served as a basis for the evaluation together with the following criteria. The results are shown in Table 8.

<Evaluation Criteria>
☐: The transmittance was 50% or more.
○: The transmittance was 30% or more and less then 50%.
☐: The transmittance was 20% or more and less then 30%.
×: The transmittance was less then 20%.

TABLE 8

| Component | Experiment 15 | Experiment 16 |
|---|---|---|
| Spherical silica (*1) | 5.0 | |
| Amorphous silica (*2) | | 5.0 |
| Cyclopolysiloxane | 30.0 | 30.0 |
| Dimethylpolysiloxane | Balance | Balance |
| Color development intensity | ☐ | ☐ |
| Transparency | ☐ | ○ |
| Transmittance | ☐ | ○ |

(*1) "P-1500" manufactured by CATALYSTS&CHEMICALS IND. CO., LTD.
(*2) amorphous(shapeless) silica anhydride(particle size: 1–3 μm).

As evident from Table 8, the use of a spherical silica powder forming a uniform continuous interface with the liquid phase gave excellent color-developing performance and transparency when compared with the use of the amorphous(shapeless) silica powder, although the both samples did develop colors and showed the transparency.

5. Amount of Powder

Each of the samples having the formulations shown in Tables 9 to 10 was prepared and examined for the relationship of the silica powder content with the color development and transparency. The color development intensity and the transparency were evaluated visually by the panelists based on the criteria similar to that described above, and the transparency was also evaluated by the method described above. The results are shown in Tables 9 to 10.

TABLE 9

| Component | Experiment 17 | Experiment 18 | Experiment 19 |
|---|---|---|---|
| Spherical silica (*1) | 0.005 | 0.1 | 10.0 |
| Cyclopolysiloxane | 30.3 | 30.5 | 30.0 |
| Dimethylpolysiloxane | Balance | Balance | Balance |
| Color development intensity | x | ○ | ☐ |
| Transparency | ☐ | ☐ | ☐ |
| Transmittance | ☐ | ☐ | ☐ |
| Refractive index of silica | 1.50 | 1.50 | 1.50 |
| Refractive index of liquid | 1.498 | 1.498 | 1.498 |

(*1) silicic anhydride(particle size: 5–8 μm).

TABLE 10

| Component | Experiment 20 | Experiment 21 |
|---|---|---|
| Spherical silica (*1) | 42.0 | 65.0 |
| Cyclopolysiloxane | 29.9 | 29.2 |
| Dimethylpolysiloxane | Balance | Balance |
| Color development intensity | ○ | x |
| Transparency | ☐ | x |
| Transmittance | ☐ | x |
| Refractive index of silica | 1.50 | 1.50 |
| Refractive index of liquid | 1.498 | 1.498 |

(*1) silicic anhydride(particle size: 5–8 μm).

As evident from Tables 9 to 10, an extremely small amount of the silica powder resulted in a difficulty in developing a color of the composition, while an excessive amount resulted in a white-turbid composition without color development or transparency. Accordingly, the amount of the silica powder to be added is preferably 0.01 to 60% by mass in view of the color development and the transparency.

In the following, preferable examples of the inventive composition as a cosmetics preparation are described.

EXAMPLE 7

Non-Alcohol Fragrance (1)

| (Component) | (Content) |
|---|---|
| Decamethylcyclopentasiloxane | 33.0 |
| Dimethylpolysiloxane | Balance |
| Perfumes | Q.S. |
| Spherical silica | 10.0 |

According to the formulation described above, a fragrance containing a powder was prepared as a cosmetic fragrance by a normal method. This composition was a transparent fragrance containing a powder capable of developing a color.

EXAMPLE 8

Non-Alcohol Type Fragrance (2)

| (Component) | (Content) |
|---|---|
| Decamethylcyclopentasiloxane | 2.0 |
| Methylphenylpolysiloxane | Balance |
| Perfumes | Q.S. |
| Spherical silica | 10.0 |

According to the formulation described above, a fragrance containing a powder was prepared as a cosmetic fragrance by a normal method. This composition was a transparent fragrance containing a powder capable of developing a color.

EXAMPLE 9

Massage Oil

| (Component) | (Content) |
|---|---|
| Liquid paraffin | 70.0 |
| Squalane | 1.0 |
| Ester oil | 20.0 |
| Decamethylcyclopentasiloxane | Balance |
| Perfumes | Q.S. |
| Spherical silica | 5.0 |

According to the formulation described above, a massage oil containing a powder was prepared as a cosmetic preparation for massage by a normal method. This composition was a transparent massage oil containing a powder capable of developing a color.

EXAMPLE 10

Overcoat Mail Enamel

| (Component) | (Content) |
|---|---|
| Spherical silica | 2.0 |
| Nitrocellulose 1/4 second(30% Isopropyl alcohol) | 15.0 |
| Nitrocellulose 1/2 second(30% IPA) | 4.0 |
| Alkyd resin(versatic acid glycidyl ester modified) | 4.0 |
| Sucrose benzoate | 4.0 |
| Silicone graft polymer("Aron GS-30"; solid base) | 2.0 |
| Sucrose acetate isobutyrate | 3.0 |
| Acetyl triethyl citrate | 5.0 |
| Isopropyl alcohol (IPA) | 3.0 |
| n-Butyl alcohol | 1.0 |
| Ethyl acetate | 25.0 |
| n-Butyl acetate | Balance |

According to the formulation described above, an overcoat nail enamel was prepared as a make-up cosmetic preparation by a normal method. This composition was a transparent make-up cosmetic preparation capable of developing a color.

EXAMPLE 11

Basecoat Nail Enamel

| (Component) | (Content) |
|---|---|
| Spherical silica | 5.0 |
| Nitrocellulose 1/4 second(30% IPA) | 7.0 |
| Nitrocellulose 1/2 second(30% IPA) | 5.0 |
| Alkyd resin(versatic acid glycidyl ester modified) | 6.0 |
| Sucrose benzoate | 6.0 |
| Silicone graft polymer("Aron GS-30"; solid base) | 2.0 |
| Sucrose acetate isobutyrate | 3.0 |
| Acetyl triethyl citrate | 5.0 |
| Isopropyl alcohol | 3.0 |
| n-Butyl alcohol | 1.0 |
| Ethyl acetate | 25.0 |
| n-Butyl acetate | Balance |

According to the formulation described above, a basecoat nail enamel was prepared as a make-up cosmetic preparation by a normal method. This composition was a transparent make-up cosmetic preparation capable of developing a color.

EXAMPLE 12

Transparent Lipstick

| (Component) | (Content) |
|---|---|
| Dextrin palmitate | 0.1 |
| 12-Hydroxystearic acid | 11.0 |
| Liquid lanolin | 5.0 |
| Methylphenylsilicone | 18.0 |
| Decamethylcyclopentasiloxane | Balance |
| Monohydrogenated rosin glyceryl diisostearate | 9.0 |
| Glyceryl tri-2-ethylhexanoate | 13.9 |
| 2-Ethylhexyl p-methoxycinnamate | 5.0 |
| Spherical silica | 3.0 |

According to the formulation described above, a transparent lipstick was prepared as a make-up cosmetic preparation by a normal method. This transparent lipstick was filled in glass plates whose light path sandwiched by 1-mm thick glass plates was adjusted at 1 mm, cooled, solidified, allowed to stand at 25° C. for 1 hour, and examined for the transmittance (% T) at 550 nm by a spectrophotometer, which was 41% T. This composition exhibited a shining color, and was a transparent solid make-up cosmetic preparation.

EXAMPLE 13

Transparent Coating Preparation (Cream Form)

| (Component) | (Content) |
|---|---|
| Decamethylcyclopentasiloxane | 21.0 |
| Methylphenylpolysiloxane | 31.5 |
| Spherical silica | 40.0 |
| Dextrin palmitate | 7.5 |

According to the formulation described above, a transparent base was prepared, which was a transparent cream capable of developing a color.

What is claimed is:

1. A color-developing composition, wherein said color-developing composition comprises a powder dispersion containing a liquid phase and a solid phase;
   wherein said solid phase comprises a spherical silica powder;
   wherein said liquid phase has a refractive index of n1 and said solid phase containing said silica has a refractive index of n2; wherein the mean particle size of the silica powder is about 0.1 μm to 200 μm; wherein said spherical silica powder containing solid phase has a refractive index of $1.3<n2<2.0$; and
   wherein said refractive index of said liquid phase is within 0.05 of said refractive index of said solid phase, which satisfies Equation (1): $|n1-n2|<0.05$ (1);
   whereby a color is developed at the interface between said liquid phase and said solid phase in said color-developing composition when said solid phase is mixed with or dispersed in said liquid phase.

2. A cosmetic preparation employing a color-developing composition according to claim 1.

3. The cosmetic preparation according to claim 2, wherein said cosmetic preparation is a skin care product, a make-up product, a fragrance product, a skin or hair cleansing product, or an enamel removing product.

4. The color-developing composition according to claim 1, wherein said liquid phase comprises polysiloxane such that said refractive index (n1) of said liquid phase is within 0.05 of said refractive index (n2) of said solid phase to satisfy said Equation (1).

5. The color-developing composition according to claim 4, wherein said polysiloxane is at least one selected from the group consisting of cyclopolysiloxane and methylphenylpolysiloxane.

6. The color-developing composition according to claim 1, wherein said liquid phase comprises one or more substances which are selected from the group consisting of oils, fats, waxes, fatty oils, alcohols and water.

7. The color-developing composition according to claim 1, wherein said liquid phase is replaced with a gel phase or a liquid crystal phase comprising one or more substances which are selected from the group consisting of oils, fats and fatty oils, waxes, alcohols and water; and wherein said color-developing composition is a powder dispersion gel or a powder dispersion liquid crystal.

8. The color-developing composition according to claim 1, wherein the spherical silica powder is contained in an amount of 0.01 to 60% by mass based on the entire composition.

9. A display article employing a color-developing composition according to claim 1.

10. A method for applying a color-developing composition according to claim 1 to a cosmetic preparation comprising:
    dispersing said solid phase in said liquid phase in said cosmetic preparation.

11. A method for applying a color-developing composition according to claim 1 to a display article comprising:
    dispersing said solid phase in said liquid phase in said display article.

12. The color-developing composition according to claim 1, wherein said spherical silica powder in said solid phase has a refractive index of $1.3<n2<1.6$.

* * * * *